United States Patent
Wayne et al.

(10) Patent No.: US 7,902,371 B2
(45) Date of Patent: Mar. 8, 2011

(54) (1S,5S)-3-(5,6-DICHLOROPYRIDIN-3-YL)-3,6-DIAZABICYCLO[3.2.0]HEPTANE BENZENESULFONATE

(75) Inventors: Gregory S. Wayne, Vernon Hills, IL (US); Sean M. Mellican, Gurnee, IL (US); Geoff G. Z. Zhang, Libertyville, IL (US); David R. Willcox, Ridgefield, CT (US); Jeffrey M. Breting, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 224 days.

(21) Appl. No.: 12/358,631

(22) Filed: Jan. 23, 2009

(65) Prior Publication Data

US 2009/0198067 A1 Aug. 6, 2009

Related U.S. Application Data

(62) Division of application No. 11/838,713, filed on Aug. 14, 2007, now Pat. No. 7,498,444, which is a division of application No. 11/176,088, filed on Jul. 7, 2005, now Pat. No. 7,351,833.

(60) Provisional application No. 60/590,677, filed on Jul. 23, 2004.

(51) Int. Cl.
*C07D 487/04* (2006.01)
(52) U.S. Cl. .................................. 546/276.7
(58) Field of Classification Search ............... 546/276.7
See application file for complete search history.

(56) References Cited

U.S. PATENT DOCUMENTS

| 2004/0242641 A1 | 12/2004 | Buckley et al. |
| 2004/0242644 A1 | 12/2004 | Buckley et al. |
| 2005/0261348 A1 | 11/2005 | Buckley et al. |
| 2006/0035936 A1 | 2/2006 | Buckley et al. |

FOREIGN PATENT DOCUMENTS

| WO | 01/81347 | 11/2001 |
| WO | 2004/106342 | 12/2004 |

OTHER PUBLICATIONS

Arneric, et al., "Cholingeric channel modulators as a novel therapeutic strategy for Alzheimer's disease," Exp. Opin. Invest. Drugs 5(1): 79-100 (1996).
Arneric, et al., "Neuronal nicotinic acetycholine receptors," Psychopharmacology: The Fourth Generation of Progress 95-110 (1995).
Brittain, et al., "Polymorphism in Pharmaceutical Solids," NY: Marcel Dekker, Inc, 185: 1-2 (1999).
Carty, et al., "Cox-2 inhibitors. Potential for reducing NSAID side-effects in treating inflammatory disease," Emerging Drugs: The Prospect for Improved Medicines, Annual Executive Briefing, Chapter 19: 391-411 (1996).
Chaplan, et al., "Quantitative assessment of tactile allodynia in the rat paw," Journal of Neuroscience Methods 53:55-63 (1994).
Cherny, et al. "Opioid Analgesics, Comparative features and prescribing guidelines," Drugs 51(5): 713-737 (1996).
Decker, et al., "Effects of ABT-418, a novel cholinergic channel ligand, on place learning in septal-lesioned rats," European Journal of Pharmacology 261:217-222 (1994).
Dray, et al., "New pharmacological strategies for pain relief," Annu. Rev. Pharmacol. Toxicol. 36:253-280 (1996).
Dray, et al., "Pharmacology of chronic pain," TiPS 15:190-197 (1994).
Kim, et al., "An experimental model for peripheral neuropathy produced by segmental spinal nerve ligation in the rat," Pain 50:355-363 (1992).
Lindstrom, et al. "Nicotinic acetylcholine receptors in health and disease," Molecular Neurobiology 15:193-222 (1997).
Lloyd, et al., "The potential of subtype-selective neuronal nicotinic acetylcholine receptor agonists as therapeutic agents," Life Sciences 62(17/18): 1601-1606 (1998).
Lukas, et al. "Expression of ganglia-type nicotinic acetylcholine receptors and nicotinic ligand binding sites by cells of the IMR-32 human neuroblastoma clonal line," Journal of Pharmacology and Experimental Therapeutics 265(1): 294-302 (1993).
Muzaffar, et al., "Polymorphism and Drug Availability," J. of Pharmacy (Lahore) 1(1): 59-66 (1979).
Pabreza, et al, "[$^3$H]cytosine binding to nicotinic cholinergic receptors in brain," Molecular Pharmacology 39:9-12 (1990).
Prescott, et al., Methods in cell biology, vol. XIV, Academic Press, New York, NY, p. 33 et seq. (1976).
U S Pharmacopeia, 1843-1844 (1995).
Williams, et al., "Beyond the tobacco debate: dissecting out the therapeutic potential of nicotine," Exp. Opin. Invest. Drugs 5(8): 1035-1045 (1996).
Williams, et al., "Emerging molecular approaches to pain therapy," Journal of Medicinal Chemistry 42(9): 1481-1500 (1999).

*Primary Examiner* — Patricia L Morris
(74) *Attorney, Agent, or Firm* — Antonia M. Holland

(57) ABSTRACT

The present invention relates to the salt (1S,5S)-3-(5,6-dichloropyridin-3-yl)-3,6-diazabicyclo[3.2.0]heptane benzenesulfonate and to methods of preparing the salt.

1 Claim, 12 Drawing Sheets

Figure 2 — Acetate

Figure 5 — Methanesulfonate

Figure 7 Sulfate

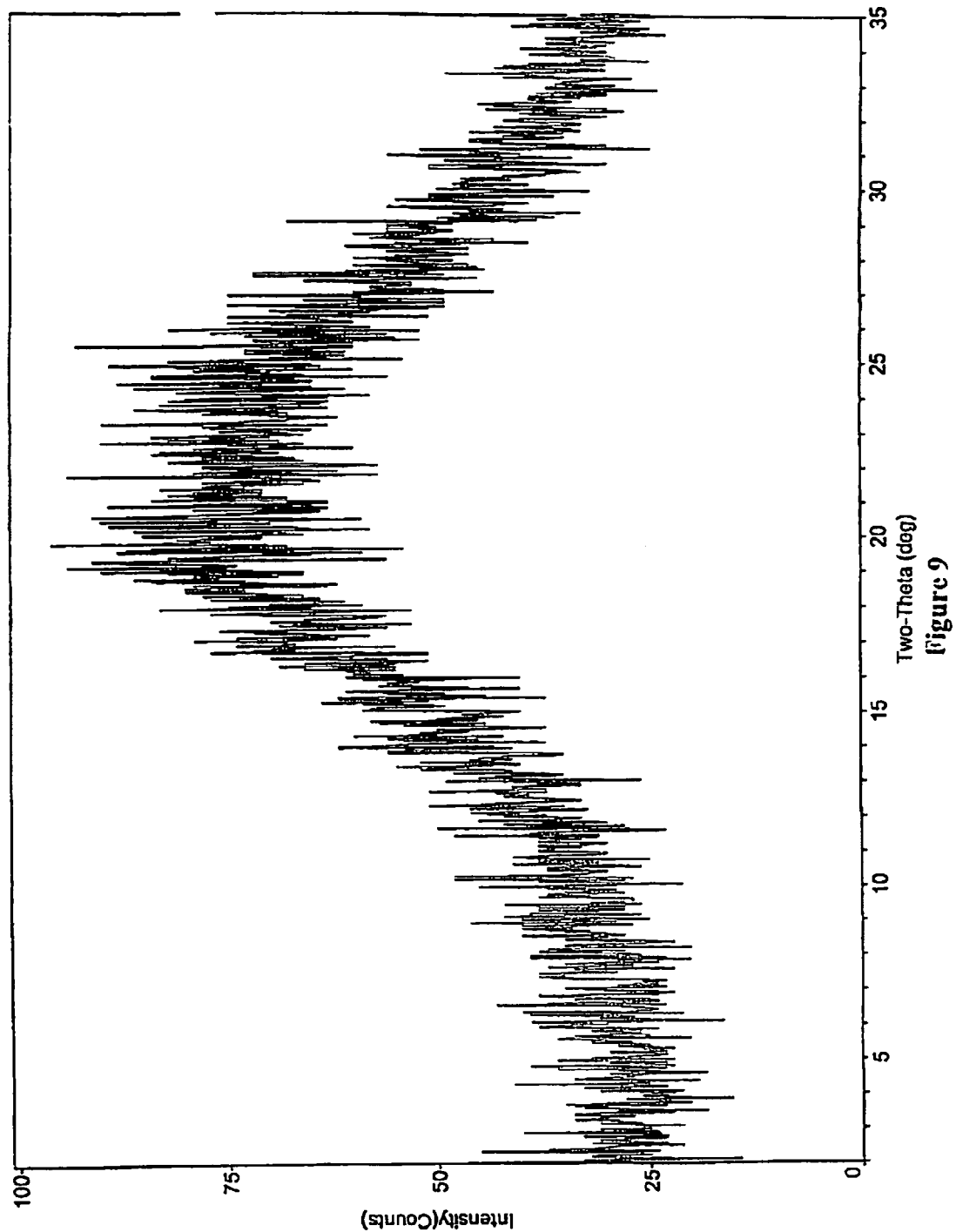

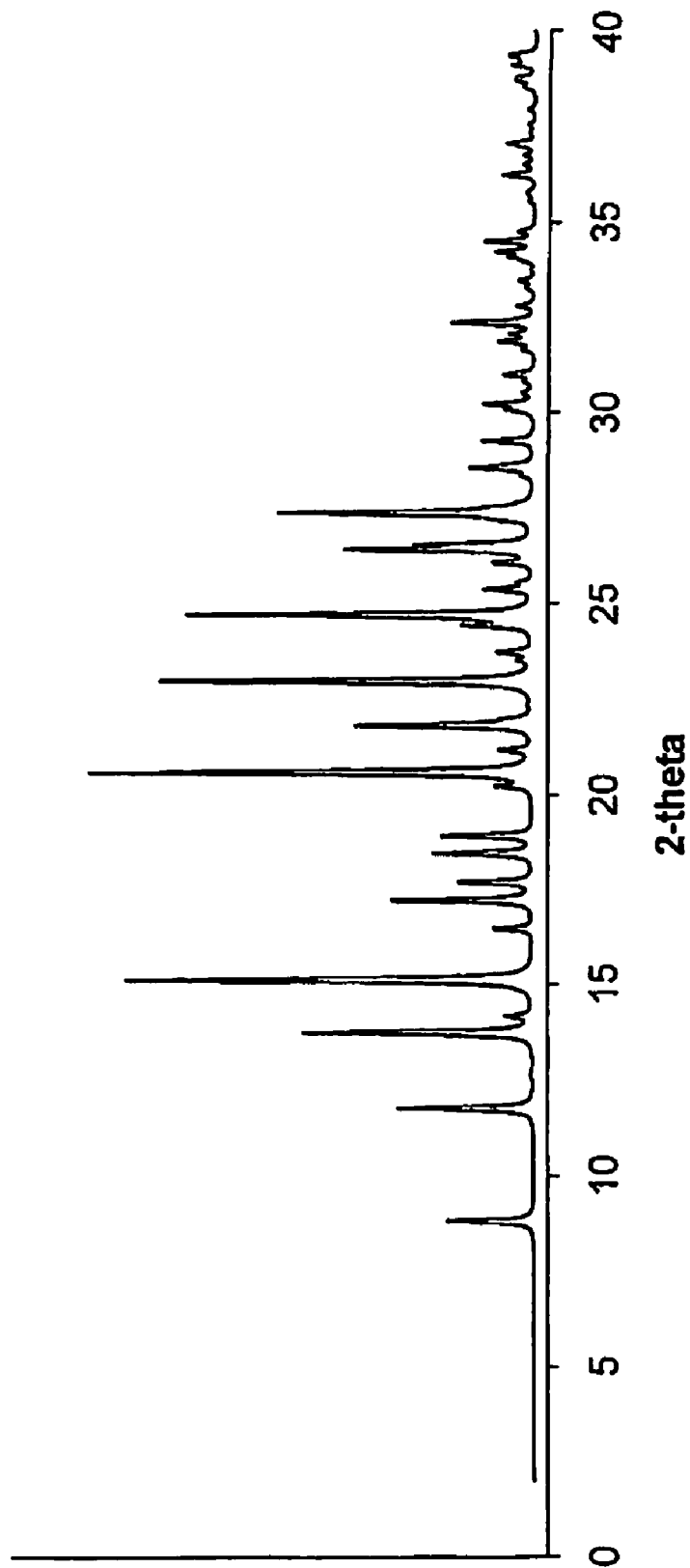

US 7,902,371 B2

(1S,5S)-3-(5,6-DICHLOROPYRIDIN-3-YL)-3,6-DIAZABICYCLO[3.2.0]HEPTANE BENZENESULFONATE

This application is a divisional of U.S. patent application Ser. No. 11/838,713, filed on Aug. 14, 2007, now U.S. Pat. No. 7,498,444 which is in turn a divisional of U.S. patent application Ser. No. 11/176,088, filed on Jul. 7, 2005, now U.S. Pat. No. 7,351,833, which claims the benefit of U.S. Patent Application No. 60/590,677, filed on Jul. 23, 2004, the entirety of each is hereby incorporated by reference.

TECHNICAL FIELD

The invention relates to the salt (1S,5S)-3-(5,6-dichloropyridin-3-yl)-3,6-diazabicyclo[3.2.0]heptane benzenesulfonate and to processes for preparing the salt.

BACKGROUND OF THE INVENTION (1S,5S)-3-(5,6-dichloropyridin-3-yl)-3,6-diazabicyclo[3.2.0]heptane is a novel compound that demonstrates utility in treating pain and disorders associated with the nicotinic acetylcholine receptor (nAChR).

(1S,5S)-3-(5,6-dichloropyridin-3-yl)-3,6-diazabicyclo[3.2.0]heptane benzenesulfonate has the same utility and has unexpected physiochemical properties such as high crystallinity, low hygroscopicity, high chemical stability, and is believed to exist as a single crystal form.

BRIEF DESCRIPTION OF THE DRAWINGS

FIG. 9 is the powder X-ray diffractogram of amorphous (1S,5S)-3-(5,6-dichloropyridin-3-yl)-3,6-diazabicyclo[3.2.0]heptane benzenesulfonate.

FIG. 10 is the powder X-ray diffractogram of crystalline (1S,5S)-3-(5,6-dichloropyridin-3-yl)-3,6-diazabicyclo[3.2.0]heptane benzenesulfonate as determined from single cell crystal data.

SUMMARY OF THE INVENTION

The present invention relates to the salt (1S,5S)-3-(5,6-dichloropyridin-3-yl)-3,6-diazabicyclo[3.2.0]heptane benzenesulfonate in an amorphous state or in a crystalline state.

In another embodiment the present invention relates to crystalline (1S,5S)-3-(5,6-dichloropyridin-3-yl)-3,6-diazabicyclo[3.2.0]heptane benzenesulfonate with characteristic peaks in the powder X-ray diffraction pattern, FIG. 10, at values of two theta of 8.8±0.2, 11.8, 13.7, 15.1, 17.2, 18.5, 18.9, 20.6, 24.4, 24.7, and 27.4±0.2.

In another embodiment, the present invention relates to substantially pure crystalline (1S,5S)-3-(5,6-dichloropyridin-3-yl)-3,6-diazabicyclo[3.2.0]heptane benzenesulfonate with characteristic peaks in the powder X-ray diffraction pattern, FIG. 10, at values of two theta of 8.8±0.2, 11.8, 13.7, 15.1, 17.2, 18.5, 18.9, 20.6, 24.4, 24.7, and 27.4±0.2.

Figure 1:
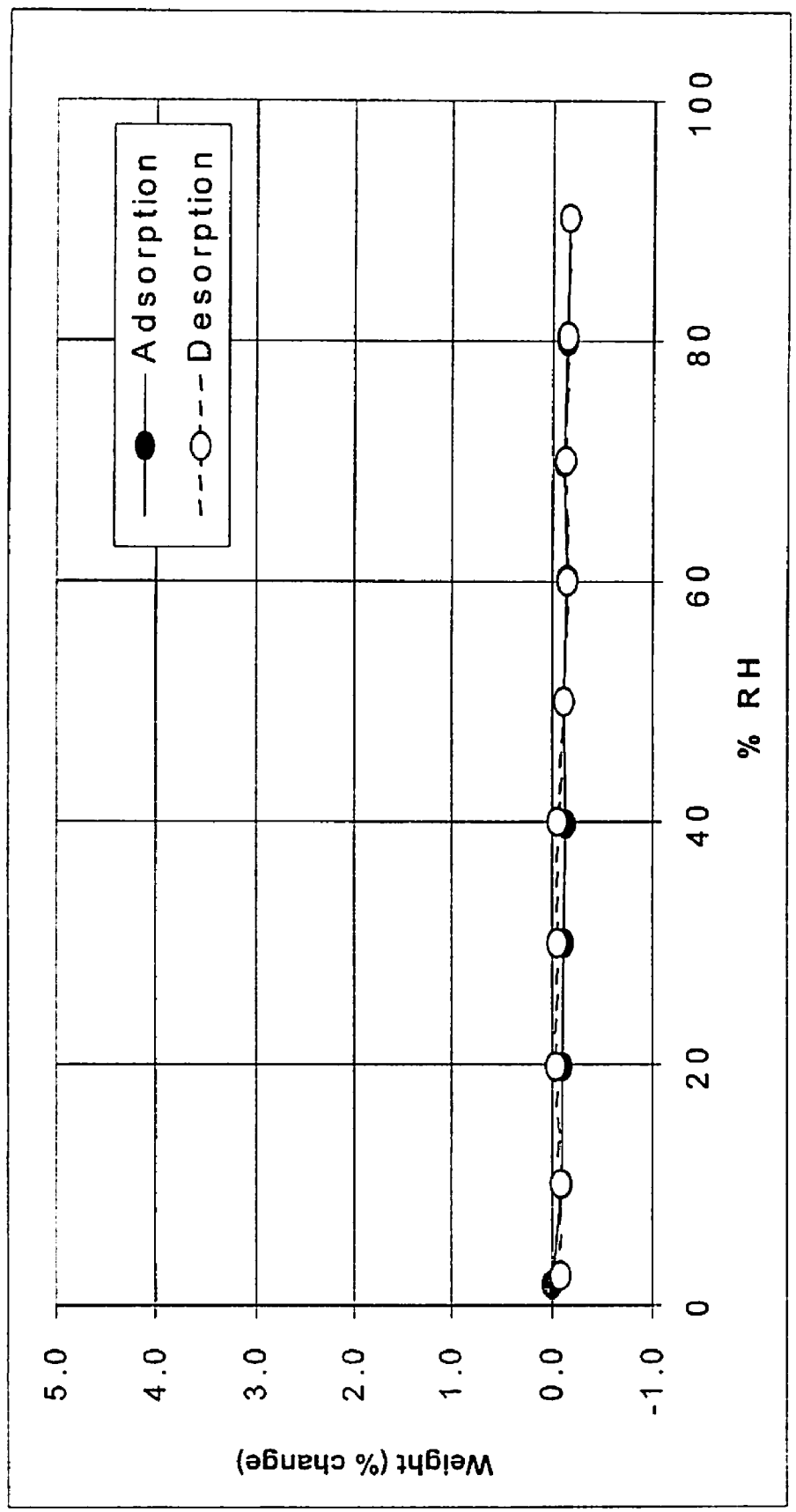
FIG. 1 is the adsorption/desorption isotherm of (1S,5S)-3-(5,6-dichloropyridin-3-yl)-3,6-diazabicyclo[3.2.0]heptane benzenesulfonate.
Figure 2:
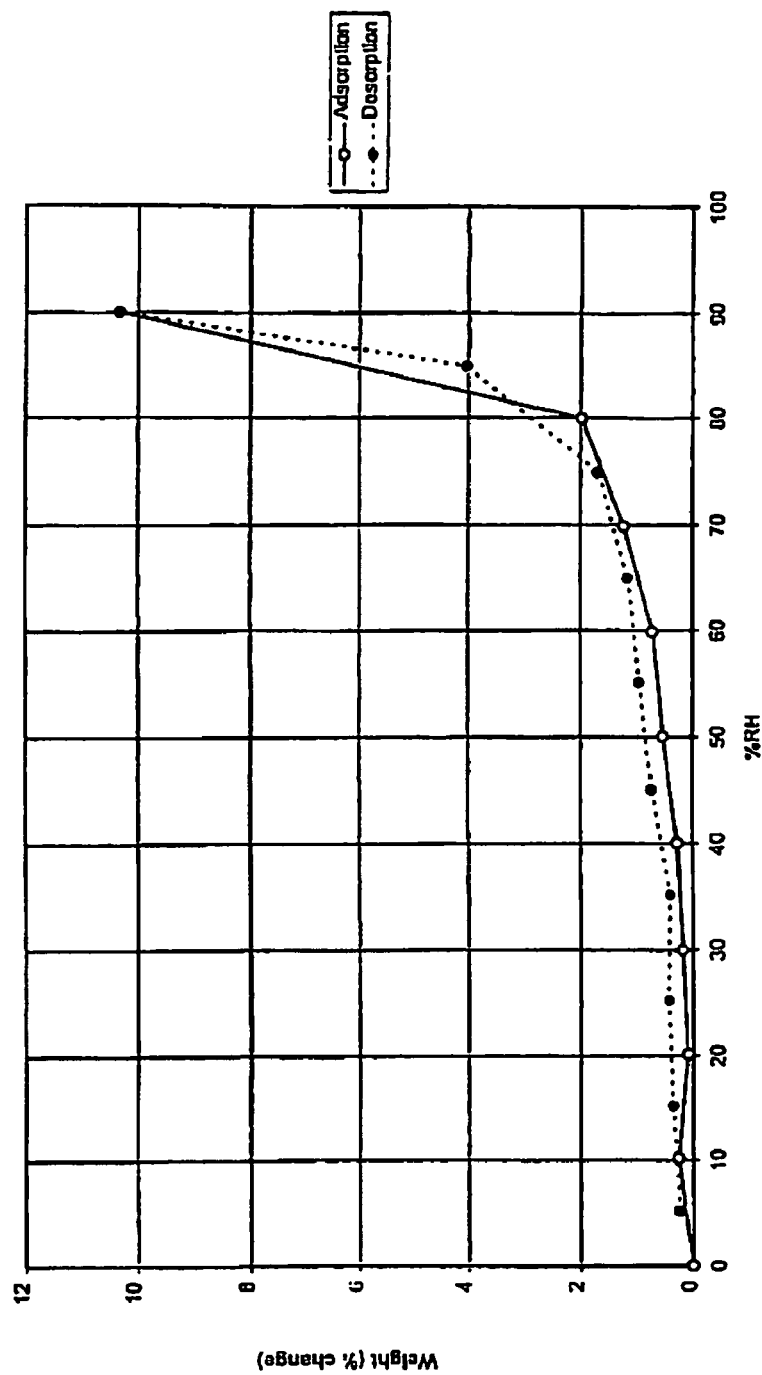
FIG. 2 is the adsorption/desorption isotherm of (1S,5S)-3-(5,6-dichloropyridin-3-yl)-3,6-diazabicyclo[3.2.0]heptane acetate.
Figure 3:
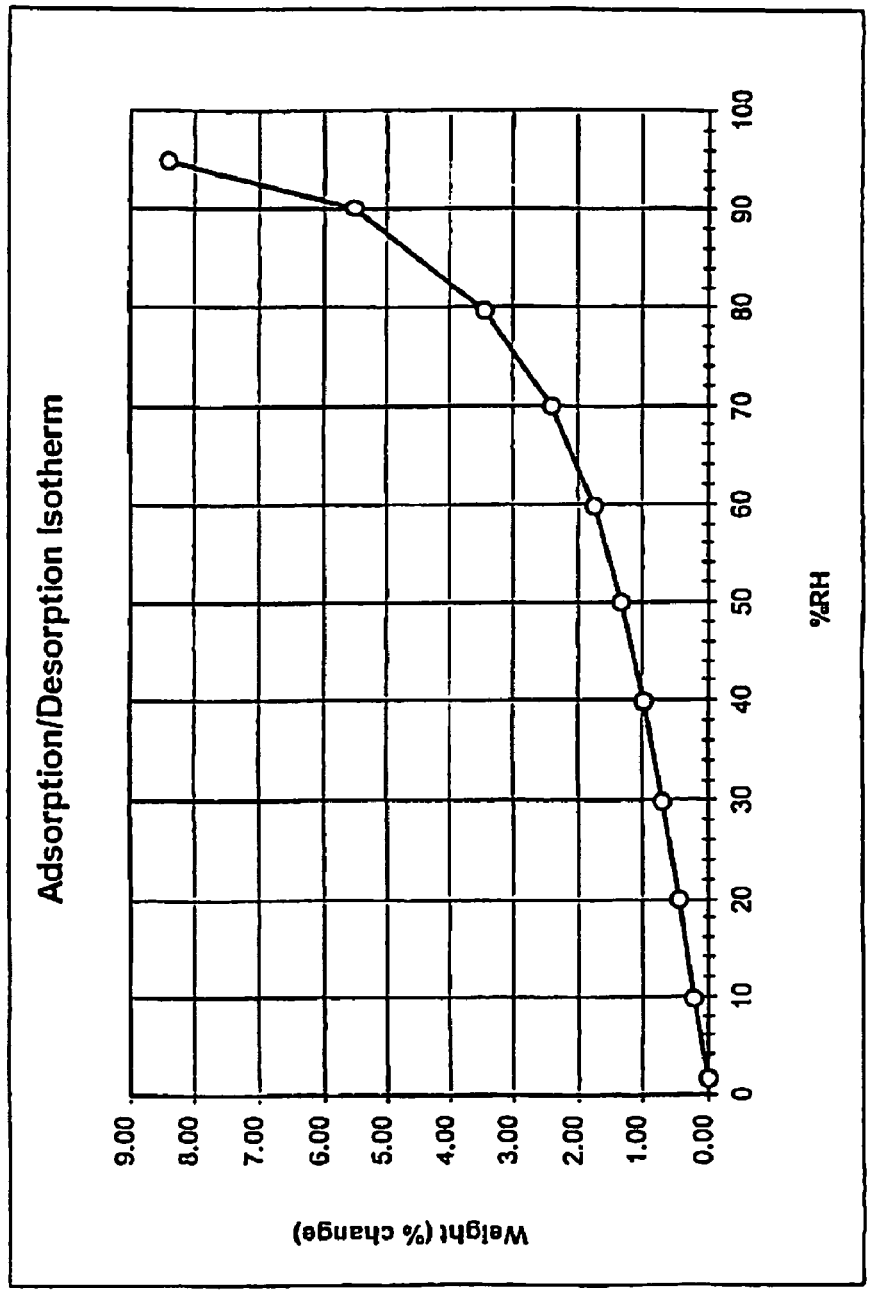
FIG. 3 is the adsorption/desorption isotherm of (1S,5S)-3-(5,6-dichloropyridin-3-yl)-3,6-diazabicyclo[3.2.0]heptane citrate.
Figure 4:
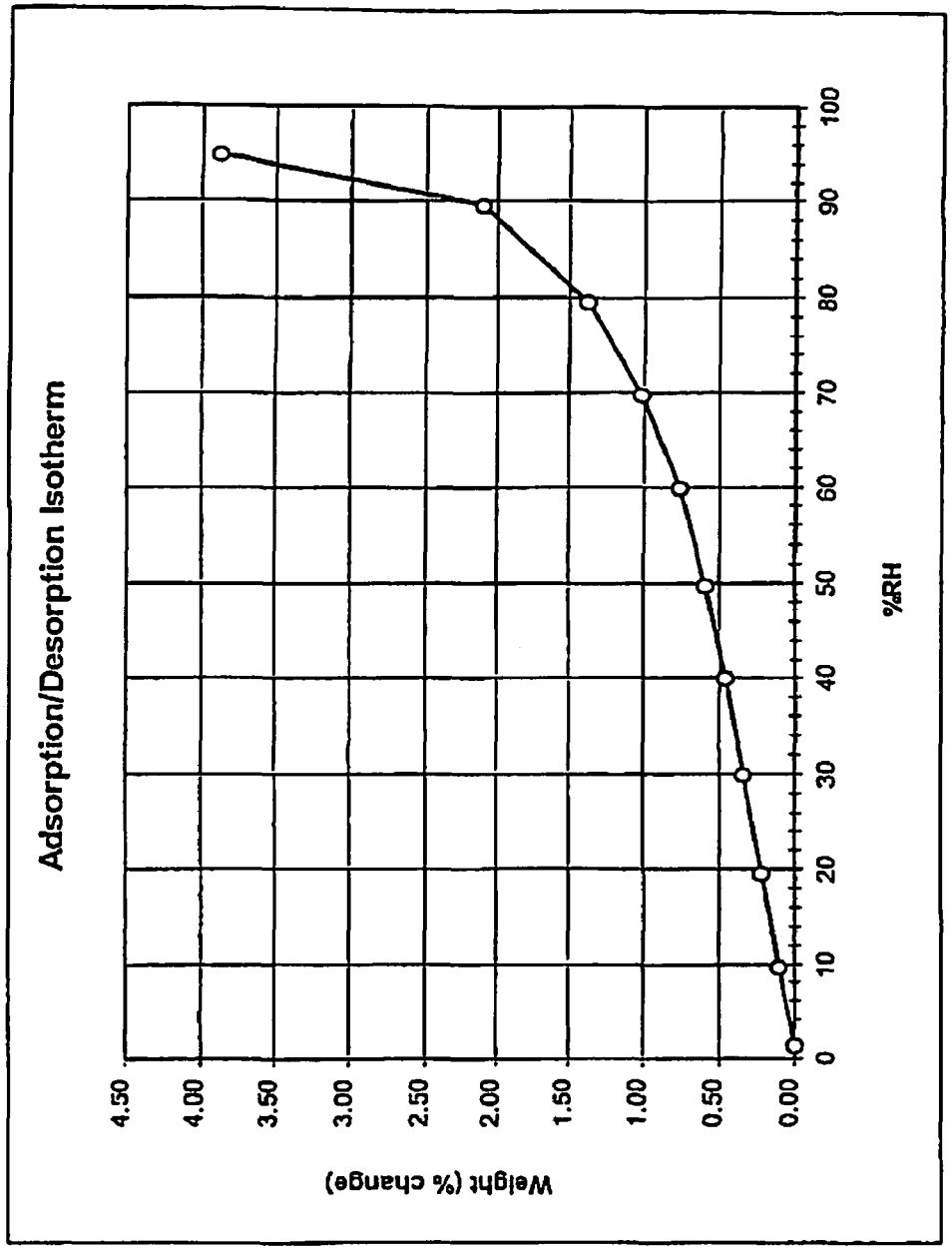
FIG. 4 is the adsorption/desorption isotherm of (1S,5S)-3-(5,6-dichloropyridin-3-yl)-3,6-diazabicyclo[3.2.0]heptane maleate.
Figure 5:
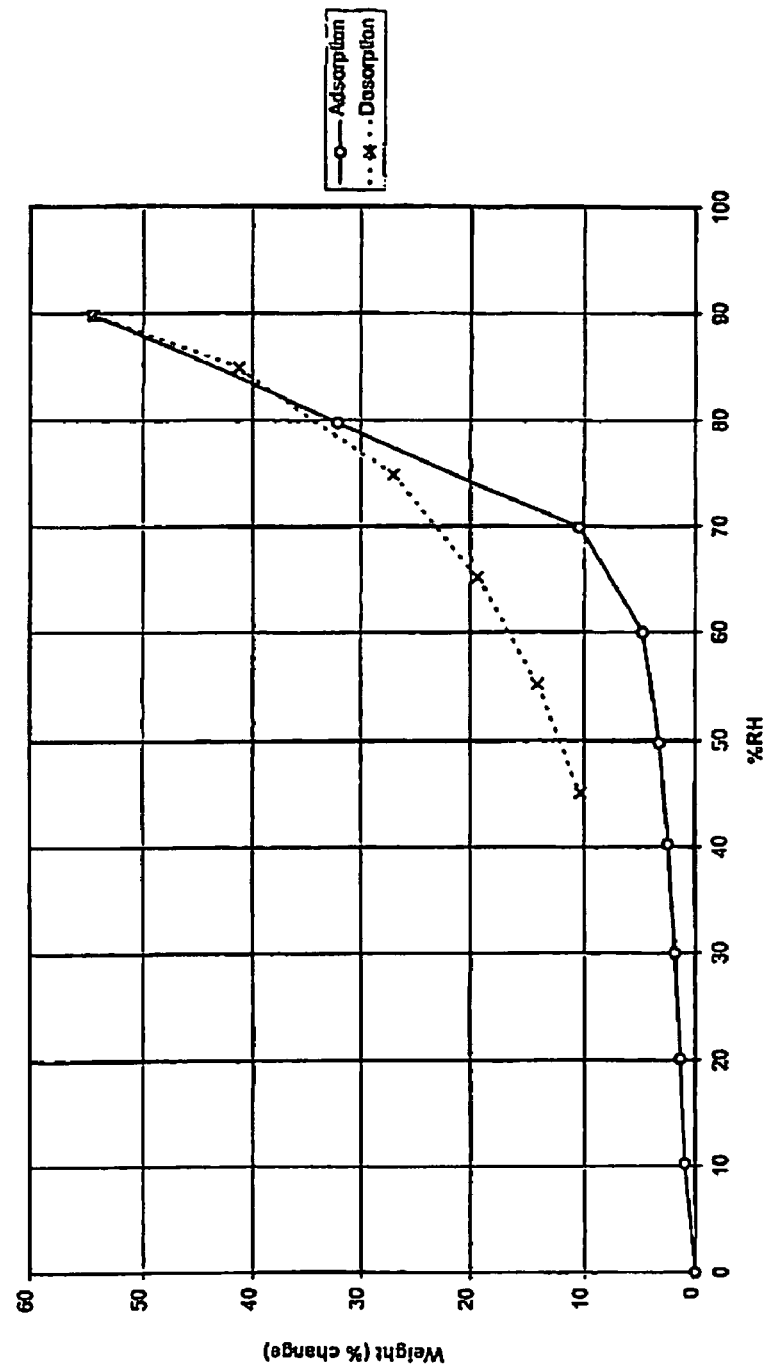
FIG. 5 is the adsorption/desorption isotherm of (1S,5S)-3-(5,6-dichloropyridin-3-yl)-3,6-diazabicyclo[3.2.0]heptane methanesulfonate.
Figure 6:
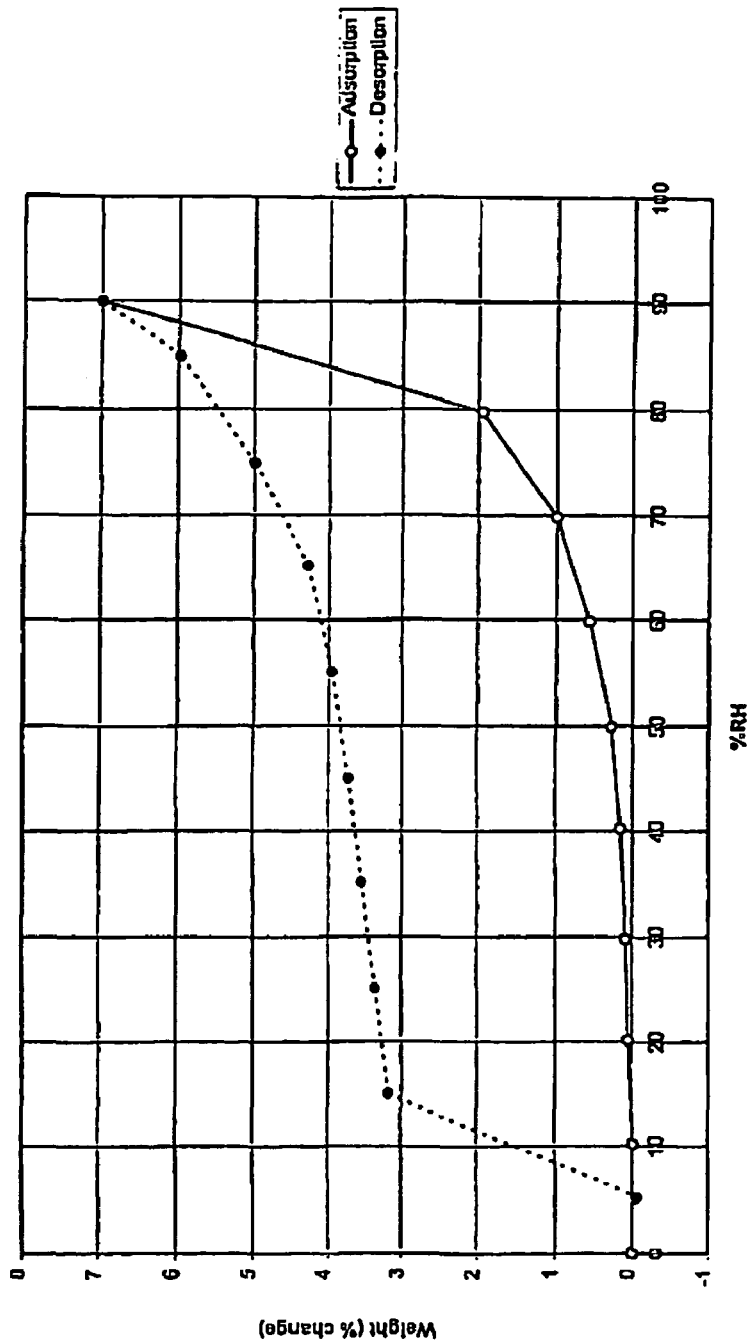
FIG. 6 is the adsorption/desorption isotherm of (1S,5S)-3-(5,6-dichloropyridin-3-yl)-3,6-diazabicyclo[3.2.0]heptane 4-methylbenzenesulfonate.
Figure 7:
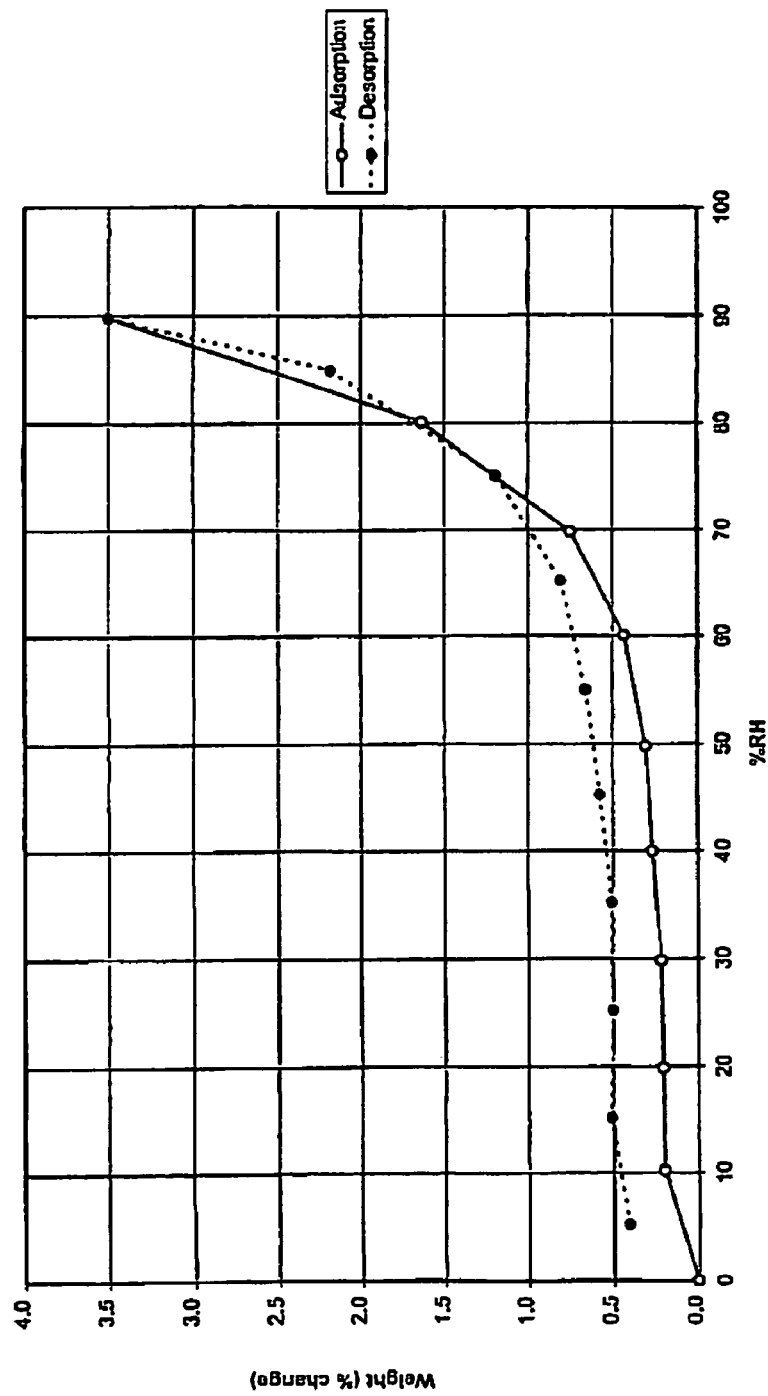
FIG. 7 is the adsorption/desorption isotherm of (1S,5S)-3-(5,6-dichloropyridin-3-yl)-3,6-diazabicyclo[3.2.0]heptane sulfate.
Figure 8:
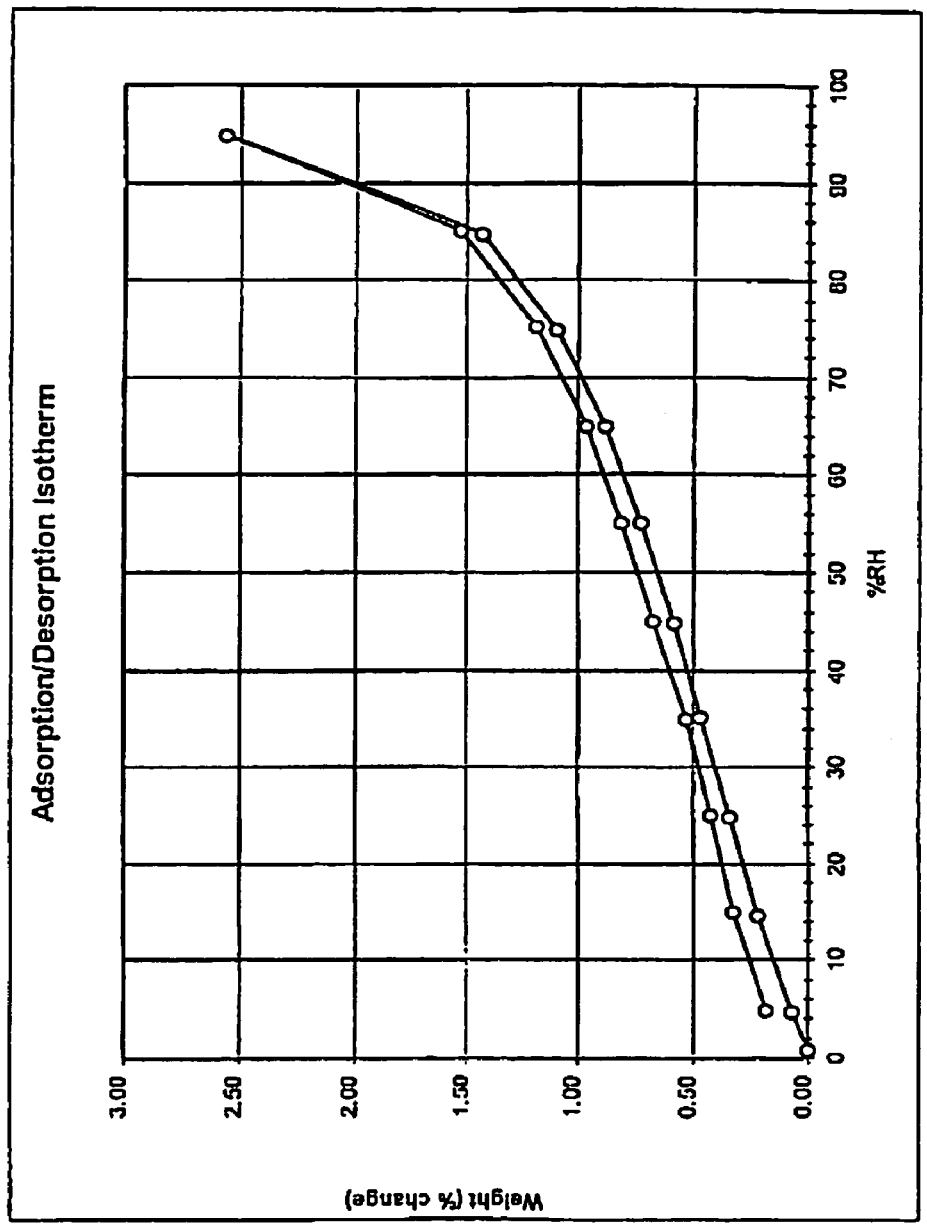
FIG. 8 is the adsorption/desorption isotherm of (1S,5S)-3-(5,6-dichloropyridin-3-yl)-3,6-diazabicyclo[3.2.0]heptane.
Figure 9A:
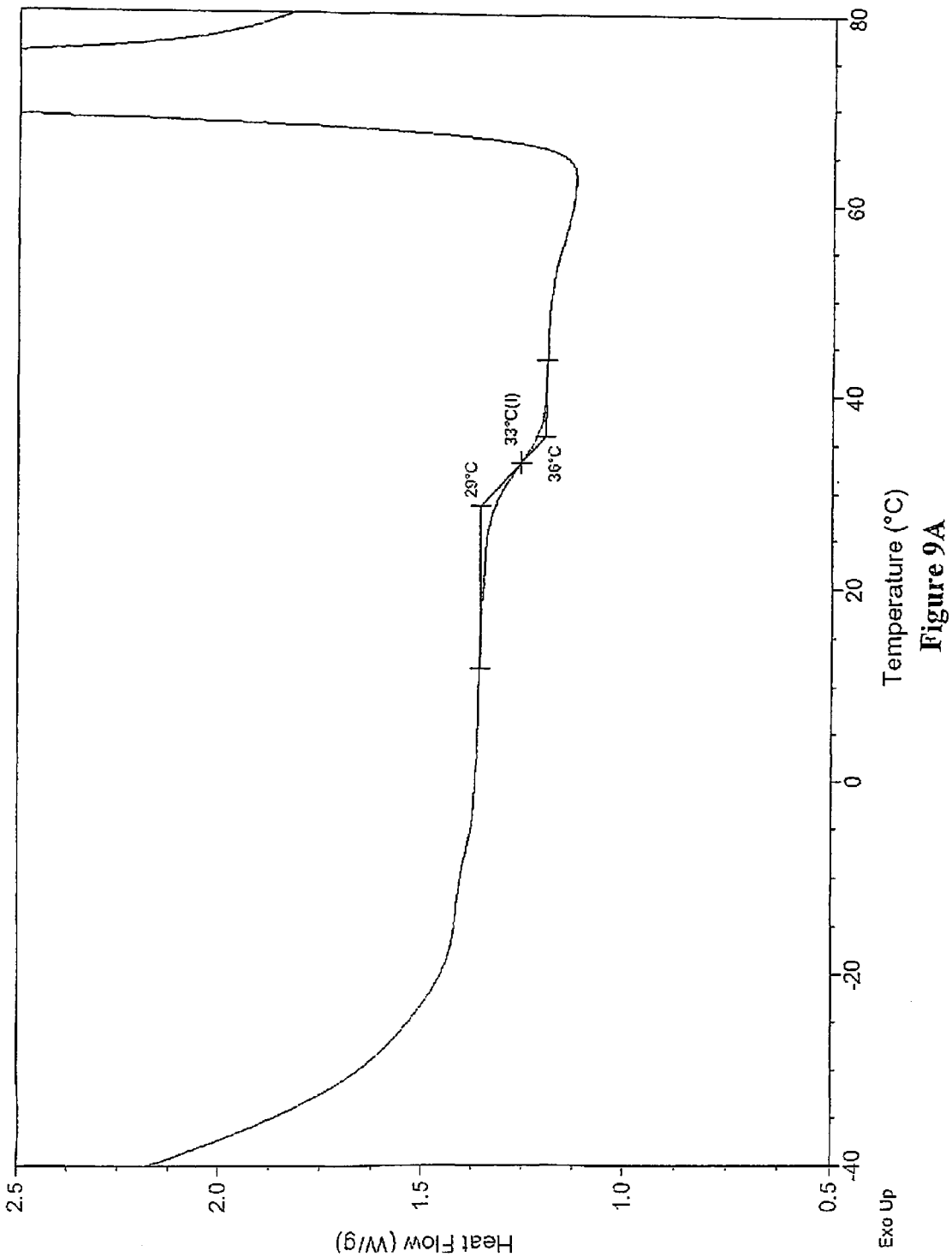
FIG. 9A is the differential scanning calorimetry thermogram of amorphous (1S,5S)-3-(5,6-dichloropyridin-3-yl)-3,6-diazabicyclo[3.2.0]heptane benzenesulfonate.

In another embodiment the present invention relates to amorphous (1S,5S)-3-(5,6-dichloropyridin-3-yl)-3,6-diazabicyclo[3.2.0]heptane benzenesulfonate, FIG. 9.

In another embodiment, the present invention relates substantially pure amorphous (1S,5S)-3-(5,6-dichloropyridin-3-yl)-3,6-diazabicyclo[3.2.0]heptane benzenesulfonate.

In another embodiment, the present invention relates to a process for preparing crystalline (1S,5S)-3-(5,6-dichloropyridin-3-yl)-3,6-diazabicyclo[3.2.0]heptane benzenesulfonate.

In another embodiment, the present invention relates to a process for preparing amorphous (1S,5S)-3-(5,6-dichloropyridin-3-yl)-3,6-diazabicyclo[3.2.0]heptane benzenesulfonate.

DETAILED DESCRIPTION OF THE INVENTION

A thermodynamic based polymorph screen was conducted with crystalline (1S,5S)-3-(5,6-dichloropyridin-3-yl)-3,6-diazabicyclo[3.2.0]heptane benzenesulfonate. The benzenesulfonate salt was suspended in different solvents including water, ethanol, acetonitrile, methanol, N,N-dimethylformamide, ethyl acetate, 1,4-dioxane, chloroform, pyridine, nitromethane, PEG 400 and 50150 v/v water/methanol. No new crystal forms were detected after three months. In contrast, multiple polymorphs were discovered for the sulfate, (L)-tartrate, and 4-methylbenzenesulfonate salts. In particular, three unique crystal forms were isolated/characterized for the 4-methylbenzenesulfonate salt versus only one for the benzenesulfonate salt. This difference between the benzenesulfonate and 4-methylbenzenesulfonate salts is unexpected considering the structural similarities of the two acids. The lack of different physical forms is an advantage to chemical and physical processing operations. This was unexpected considering most organic solids exhibit polymorphism or pseudo-polymorphism such as, for example, solvates, hydrates, and de-solvated forms.

Crystalline (1S,5S)-3-(5,6-dichloropyridin-3-yl)-3,6-diazabicyclo[3.2.0]heptane benzenesulfonate is a superior salt to the other salts of (1S,5S)-3-(5,6-dichloropyridin-3-yl)-3,6-diazabicyclo[3.2.0]heptane based on physicochemical properties such as high crystallinity of the crystalline salt, low hygroscopicity, high chemical stability, and has no known polymorphs. This was not expected considering other salts showed unfavorable properties related to crystallinity, hygroscopicity, stability, and polymorphism.

(1S,5S)-3-(5,6-Dichloropyridin-3-yl)-3,6-diazabicyclo[3.2.0]heptane benzenesulfonate exists as an amorphous solid, shown in FIG. 9, or as a crystalline solid characterized by the powder X-ray diffraction pattern shown in FIG. 10. The crystallographic unit cell parameters of (1S,5S)-3-(5,6-dichloropyridin-3-yl)-3,6-diazabicyclo[3.2.0]heptane benzenesulfonate have been determined as having the following parameters: a is 8.4 Å; b is 12.5 Å; and c is 16.9 Å, or more precisely where a is 8.391(1) Å; b is 12.488(2) Å; and c is 16.949(2) Å. To afford a cell volume of 1775 Å$^3$, or more precisely 1775.9(3) Å$^3$, wherein a, b, and c are each a representative length of the crystal lattice. The salt crystallizes in the orthorhombic P2$_1$2$_1$2$_1$ space group.

It is understood that (1S,5S)-3-(5,6-dichloropyridin-3-yl)-3,6-diazabicyclo[3.2.0]heptane benzenesulfonate crystalline solid can be identified by characteristic peaks in its powder X-ray diffraction pattern. One with skill in the art in analytical chemistry would be able to readily identify (1S,5S)-3-(5,6-dichloropyridin-3-yl)-3,6-diazabicyclo[3.2.0]heptane benzenesulfonate crystalline solid by as few as one characteristic peak in the powder X-ray diffraction pattern.

Figure 10A:
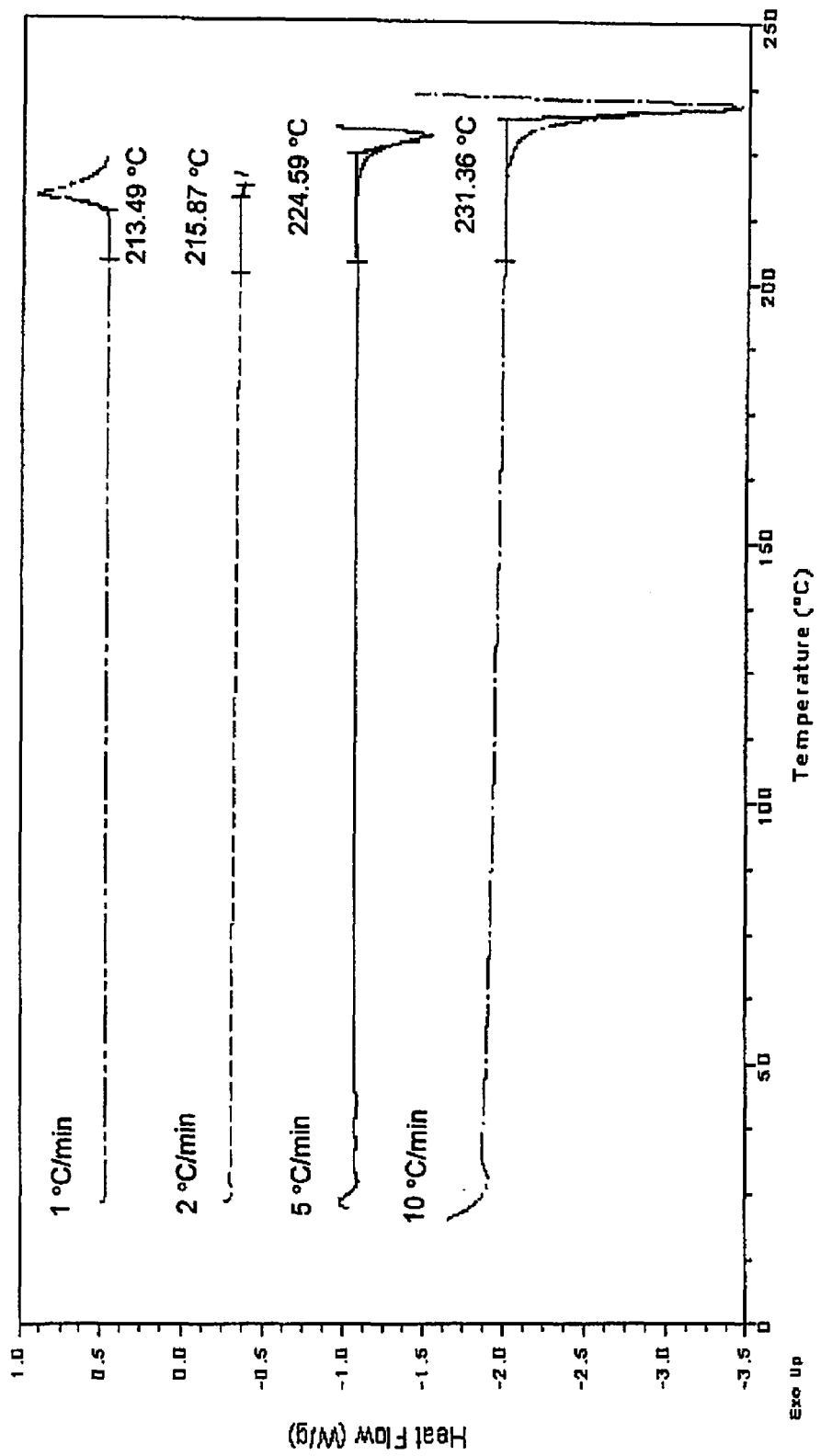
FIG. 10A shows differential scanning calorimetry thermograms of crystalline (1S,5S)-3-(5,6-dichloropyridin-3-yl)-3,6-diazabicyclo[3.2.0]heptane benzenesulfonate when heated at 1° C., 2° C., 5° C., and 10° C.

Crystalline (1S,5S)-3-(5,6-dichloropyridin-3-yl)-3,6-diazabicyclo[3.2.0]heptane benzenesulfonate undergoes decomposition initiated melting at 225° C. The decomposition/melting of crystalline (1S,5S)-3-(5,6-dichloropyridin-3-yl)-3,6-diazabicyclo[3.2.0]heptane benzenesulfonate is shown in FIG. 10A.

Crystalline (1S,5S)-3-(5,6-dichloropyridin-3-yl)-3,6-diazabicyclo[3.2.0]heptane benzenesulfonate demonstrated lower hygroscopicity relative to other salts such as the acetate, citrate, maleate, methanesulfonate, 4-methylbenzenesulfonate, and sulfate as shown by FIGS. 1-7.

Crystalline (1S,5S)-3-(5,6-dichloropyridin-3-yl)-3,6-diazabicyclo[3.2.0]heptane benzenesulfonate was tested for solid state stability at 40° C. in the dark at 75% relative humidity. The results in Table 1 demonstrate crystalline (1S,5S)-3-(5,6-dichloropyridin-3-yl)-3,6-diazabicyclo[3.2.0] heptane benzenesulfonate's chemical stability in the solid state over a 12 week period.

TABLE 1

| 75% RH, 40° C., dark | % remaining |
|---|---|
| 0 week | 99.72 ± 0.56 |
| 1 week | 100.66 ± 0.51 |
| 2 week | 99.47 ± 1.72 |
| 4 week | 100.22 ± 0.59 |
| 6 week | 100.53 ± 0.20 |
| 8 week | 100.93 ± 0.37 |
| 12 week | 100.84 ± 0.47 |

Apart from demonstrating beneficial solid state stability when exposed to heat, the benzenesulfonate salt also demonstrated beneficial chemical stability when exposed to light, i.e., photo stability, as well:

| Light | Recovery (%) |
|---|---|
| Visible light | 99.59 ± 0.69 |
| UV + Visible light | 100.25 ± 0.39 |

The benzenesulfonate salt also has high and relatively pH-independent intrinsic dissolution rates at 37° C.: pH 1.0: 8.5 mg/min·cm$^2$; pH 6.8: 10.1 mg/min·cm$^2$.

As used herein, the term "substantially pure", when used in reference to the salt (1S,5S)-3-(5,6-dichloropyridin-3-yl)-3,6-diazabicyclo[3.2.0]heptane benzenesulfonate, refers to that salt which is greater than about 90% pure. The crystalline form of (1S,5S)-3-(5,6-dichloropyridin-3-yl)-3,6-diazabicyclo[3.2.0]heptane benzenesulfonate does not contain more than about 10% of any other compound and, in particular, does not contain more than about 10% of any other form of (1S,5S)-3-(5,6-dichloropyridin-3-yl)-3,6-diazabicyclo[3.2.0]heptane benzenesulfonate, such as amorphous, solvated forms, non-solvated forms, desolvated forms, and the enantiomer. More preferably, the term "substantially pure" refers to a (1S,5S)-3-(5,6-dichloropyridin-3-yl)-3,6-diazabicyclo[3.2.0]heptane benzenesulfonate which is greater than about 95% pure. In such form, the (1S,5S)-3-(5,6-dichloropyridin-3-yl)-3,6-diazabicyclo[3.2.0]heptane benzenesulfonate does not contain more than about 5% of any other compound and, in particular, any other form of (1S,5S)-3-(5,6-dichloropyridin-3-yl)-3,6-diazabicyclo[3.2.0]heptane benzenesulfonate, such as amorphous, solvated forms, non-solvated forms, desolvated forms, and the enantiomer. Even more preferably, the term "substantially pure" refers to a (1S,5S)-3-(5,6-dichloropyridin-3-yl)-3,6-diazabicyclo[3.2.0]heptane benzenesulfonate which is greater than about 97% pure. In such salt, the (1S,5S)-3-(5,6-dichloropyridin-3-yl)-3,6-diazabicyclo[3.2.0]heptane benzenesulfonate contains no more than 3% of any other compound and, in particular, does not contain more than 3% of any other form of (1S,5S)-3-(5,6-dichloropyridin-3-yl)-3,6-diazabicyclo[3.2.0]heptane benzenesulfonate, such as amorphous, solvated forms, non-solvated forms, desolvated forms, and the enantiomer.

Yet even more preferably, the term "substantially pure" refers to a (1S,5S)-3-(5,6-dichloropyridin-3-yl)-3,6-diazabicyclo[3.2.0]heptane benzenesulfonate which is greater than about 99% pure. The (1S,5S)-3-(5,6-dichloropyridin-3-yl)-3,6-diazabicyclo[3.2.0]heptane benzenesulfonate contains no more than about 1% of any other compound and, in particular, any other form of (1S,5S)-3-(5,6-dichloropyridin-3-yl)-3,6-diazabicyclo[3.2.0]heptane benzenesulfonate, such as amorphous, solvated forms, non-solvated forms, desolvated forms, and the enantiomer.

Powder X-ray diffraction (PXRD) analysis of samples was conducted in the following manner. Samples for X-ray diffraction analysis were prepared by spreading the sample powder (ground to a fine powder with mortar and pestle, or with glass microscope slides for limited quantity samples) in a thin layer on the sample holder and gently flattening the sample with a microscope slide. Samples were run in one of three configurations: circular bulk holder, a quartz zero background plate or hot stage mount (similar mounting to a zero background plate). Diffraction patterns were collected using an Inel G3000 diffractometer equipped with an incident beam germanium monochromator to provide Cu—K$_{\alpha_1}$ radiation. The X-ray generator was operated at a voltage of 40 kV and a current of 30 mA. The Inel G3000 is equipped with a position sensitive detector that monitors all diffraction data simultaneously. The detector was calibrated by collecting the attenuated direct beam for seven seconds in 1 degree intervals across a 90 degree two theta range. The calibration was checked against a silicon line position reference standard (NIST 640c). Samples were placed on an aluminum sample holder and leveled with a glass slide.

Alternatively, X-ray powder diffraction can be performed using a Rigaku Miniflex diffractometer (30 kV and 15 mA; X-ray source: Cu; Range: 2.00-40.00° Two Theta; Scan Rate: 5 degree/minute) or a Scintag X1 or X2 diffractometer (2 kW normal focus X-ray tube with either a liquid nitrogen or Peltier cooled germanium solid state detector; 45 kV and 40 mA; X-ray source: Cu; Range: 2.00-40.00° Two Theta; Scan Rate: 1 degree/minute).

Characteristic powder X-ray diffraction pattern peak positions are reported for salts in terms of angular positions (two theta) with an allowable variability of ±0.2°. The allowable variability is specified in the U.S. Pharmacopeia, pages 1843-1844 (1995). The variability of ±0.1° is intended to be used when comparing two powder X-ray diffraction patterns. In practice, if a diffraction pattern peak from one pattern is assigned a range of angular positions (two theta) which is the measured peak position ±0.2° and a diffraction pattern peak from another pattern is assigned a range of angular positions (two theta) which is the measured peak position ±0.2° and if those ranges of peak positions overlap, then the two peaks are considered to have the same angular position (two theta). For example, if a diffraction pattern peak from one pattern is determined to have a peak position of 5.20°, for comparison purposes the allowable variability allows the peak to be assigned a position in the range of 5.00°-5.40°. If a comparison peak from the other diffraction pattern is determined to have a peak position of assigned a position in the range of 5.15°-5.55°. Because there is overlap between the two ranges of peak positions (i.e., 5.00°-5.40° and 5.15°-5.55°) the two peaks being compared are considered to have the same angular position (two theta).

Single Crystal X-ray diffraction analysis of samples was conducted in the following manner. Samples for X-ray diffraction analysis were prepared by affixing selected single crystals to glass pins with epoxy adhesive. X-ray diffraction data was collected using a Bruker SMART system with an APEX area detector (50 kV and 40 mA; X-ray source: Mo). Data were collected at −90° C.

Relative humidity isotherms were collected using a VTI SGA-100 Symmetric Vapor Sorption Analyzer. About 2 to 30 mg of sample is added to the system. The relative humidity is held constant at each step until a constant weight equilibrium is achieved or a maximum of six hours per step.

A TA Instruments Q 1000 DSC was used to determine the melt properties of the compounds. The samples were heated at 5 or 10° C./min from approximately room temperature until past the decomposition/melt temperature. The data was analyzed using TA Instruments Universal Analysis software.

Differential scanning calorimetric (DSC) analysis of samples was conducted in the following manner. A T.A. Instruments Model Q1000 differential scanning calorimeter using standard software to identify the onset of the melt. The analysis parameters were: sample weight 1-3 mg, placed in an aluminum pan, and sealed after a pin hole was poked in the lid; heating rate: 10° C./minute). The amorphous material was weighed into a stainless steel high pressure pan and sealed in a dry box. The heating rate was 20° C./minute.

One process for preparing (1S,5S)-3-(5,6-dichloropyridin-3-yl)-3,6-diazabicyclo[3.2.0]heptane benzenesulfonate is shown below in Scheme 1.

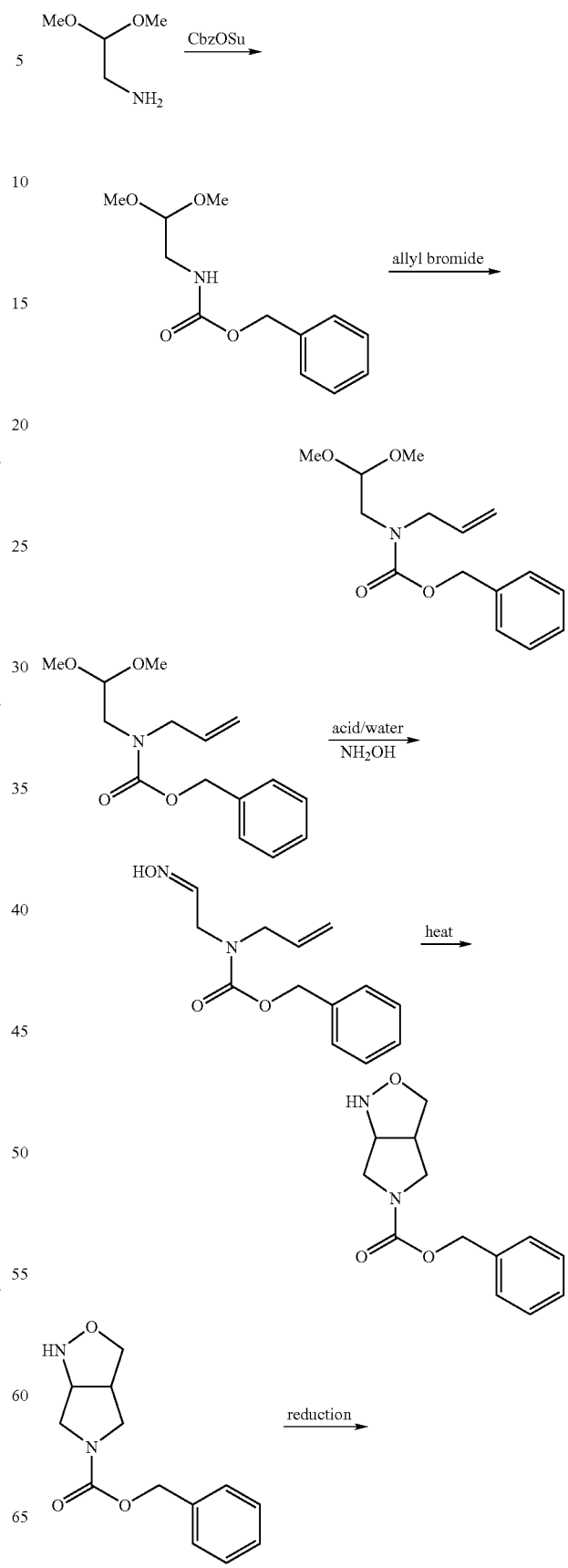

Scheme 1

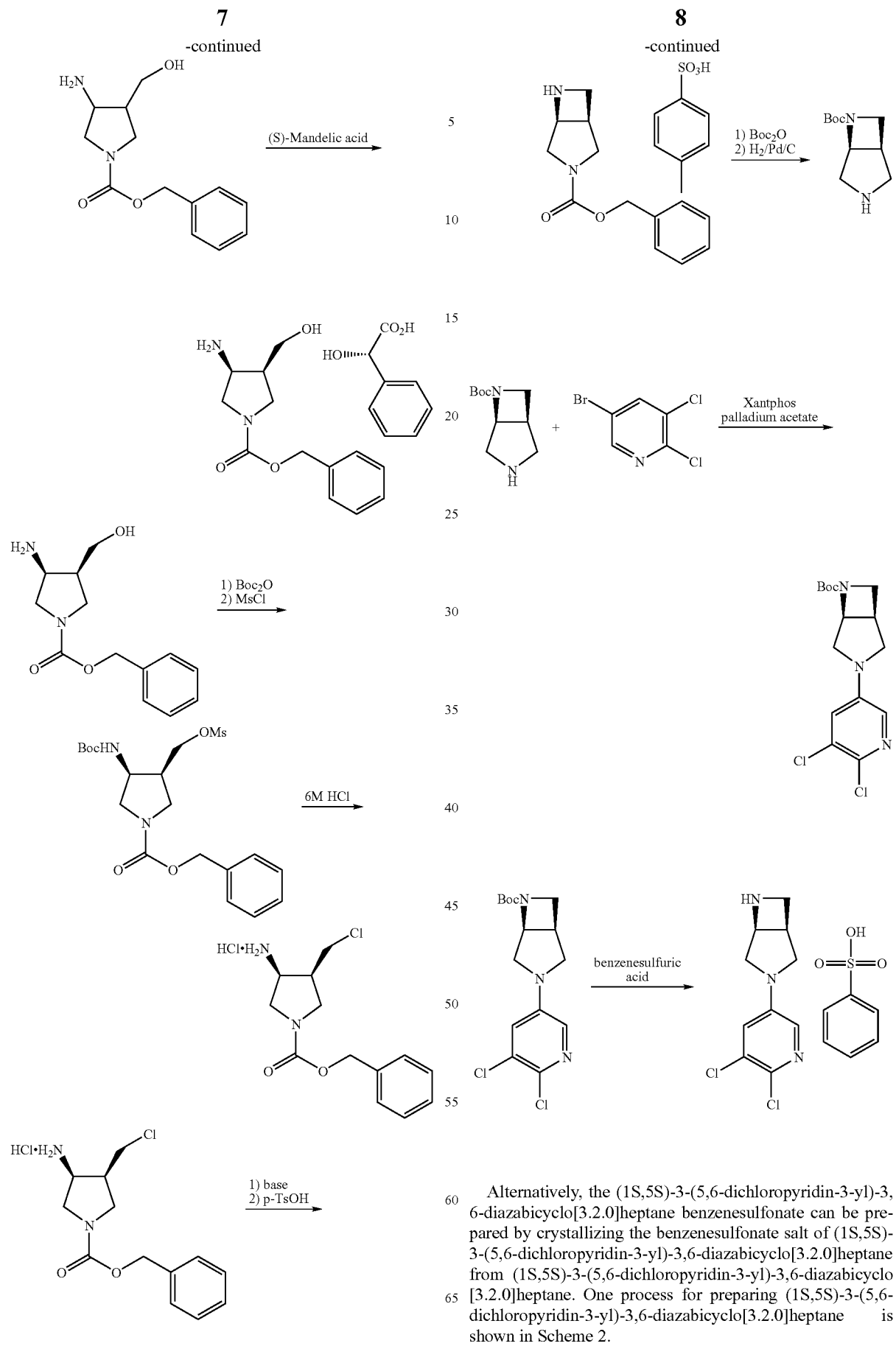
Alternatively, the (1S,5S)-3-(5,6-dichloropyridin-3-yl)-3,6-diazabicyclo[3.2.0]heptane benzenesulfonate can be prepared by crystallizing the benzenesulfonate salt of (1S,5S)-3-(5,6-dichloropyridin-3-yl)-3,6-diazabicyclo[3.2.0]heptane from (1S,5S)-3-(5,6-dichloropyridin-3-yl)-3,6-diazabicyclo[3.2.0]heptane. One process for preparing (1S,5S)-3-(5,6-dichloropyridin-3-yl)-3,6-diazabicyclo[3.2.0]heptane is shown in Scheme 2.

Scheme 2

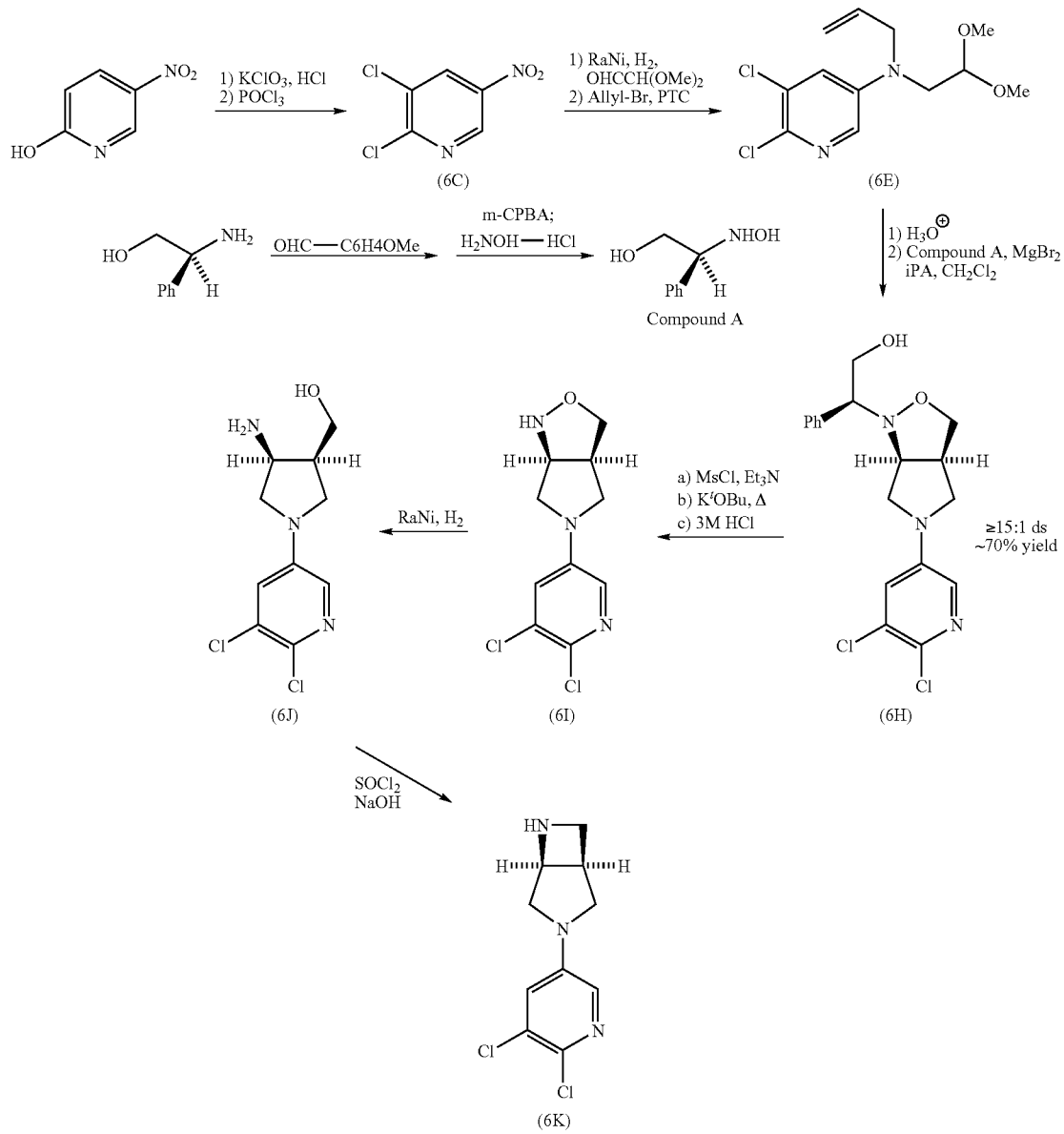

As shown in Scheme 2, the sequential treatment of 2-hydroxy-5-nitropyridine with potassium chlorate under heated conditions provides 3-chloro-2-hydroxy-5-nitropyridine which when further treated with phosphorous oxychloride under heated conditions provides 2,3-dichloro-5-nitropyridine. The nitro containing compound when treated to the reductive conditions of Raney-nickel and 40 PSI of hydrogen provides the amine which when further treated with glyoxal-1,2-dimethyl acetal in the presence of Raney-nickel under heated condition provides (5,6-dichloro-pyridin-3-yl)-(2,2-dimethoxy-ethyl)-amine. The amine when treated with allyl bromide and methyl tributyl ammonium chloride in a mixture of methyl tert-butyl ether and 50% aqueous sodium hydroxide provides allyl-(5,6-dichloro-pyridin-3-yl)-(2,2-dimethoxy-ethyl)amine (Compound 6E).

The synthesis of compound of formula A wherein the phenyl group may be optionally substituted with groups such as alkyl, alkoxy or halo may be achieved according to the following pathway. (S)-phenylglycinol (or a substituted version) when treated with p-anisaldehyde in methyl tert-butyl ether under reflux condition under a Dean-Stark trap followed by cooling to 0° C., diluting with a solvent such as tetrahydrofuran and treating with m-chloroperoxybenzoic acid and hydroxylamine provides compounds of formula A.

The treatment of Compound 6E with an acid such as hydrochloric acid under cooling conditions provides (allyl-5,6-dichloro-pyridin-3-yl)-amino)-acetaldehyde which when treated with 2-(S)-hydroxyamino-2-phenyl-ethanol and magnesium bromide in a solvent such as isopropyl alcohol provides (3S,4S)-2-[5-(5,6-dichloro-pyridin-3-yl)-hexahydropyrrolo[3,4-c]isoxazol-1-yl]-2-(2'S)-phenyl-ethanol (Compound 6H). Compound 6H when treated with methanesulfonyl chloride to generate the mesylate which is then treated with sodium tert-butoxide followed by an acidic workup provides (3S,4S)-5-(5,6-dichloro-pyridin-3-yl)-hexahydro-pyrrolo[3,4-c]isoxazole (Compound 61). The treatment of Compound 61 with Raney-nickel and 40 PSI of hydrogen in a mixture of tetrahydrofuran, ethanol and water provides (3S,4S)-[4-amino-1-(5,6-dichloro-pyridin-3-yl)-pyrrolidin-3-yl]-methanol (Compound 6J). The treatment of Compound 6J with thionyl chloride and N-methylpyrrolidinone under heated conditions in 1,2-dimethoxyethane followed by treatment with sodium hydroxide or another similar base provides (1S,5S)-3-(5,6-dichloropyridin-3-yl)-3,6-diaza-bicyclo[3.2.0]heptane (Compound 6K).

Hydroxyl groups described in the processes may be converted into a leaving group when necessary during the synthesis of other described compounds or as needed according to one skilled in the art to assist conversion into another functional group. Some of the methods contemplated include but are not limited to the treatment of alcohols with reagents such as methane sulfonyl chloride, trifluoromethane sulfonyl chloride, p-toluenesulfonyl chloride, thionyl chloride, methane sulfonyl anhydride, trifluoromethane sulfonyl anhydride. These transformation may be carried out in the presence of a base in a solvent such as but not limited to tetrahydrofuran or dichloromethane. Typical bases useful for these transformation include but are not limited to triethylamine, N-methylmorpholine, ethyl diisopropylamine and those known to one skilled in the art.

To prepare (1S,5S)-3-(5,6-dichloropyridin-3-yl)-3,6-diazabicyclo[3.2.0]heptane benzenesulfonate, (1S,5S)-3-(5,6-dichloropyridin-3-yl)-3,6-diazabicyclo[3.2.0]heptane can be dissolved in a solvent, preferably at about room temperature, which for the purpose of this application is 25° C. Preferably, the solvent is an alcohol, for example methanol, ethanol, 1-propanol, or isopropanol. The solvent can be used alone or as a mixture of suitable solvents, and can, but need not, contain up to 50% water. One example of a preferred solvent mixture is 95% ethanol/5% methanol.

Benzenesulfonic acid dissolved in a solvent is reacted with (1S,5S)-3-(5,6-dichloropyridin-3-yl)-3,6-diazabicyclo[3.2.0]heptane to prepare the (1S,5S)-3-(5,6-dichloropyridin-3-yl)-3,6-diazabicyclo[3.2.0]heptane benzenesulfonate salt. Generally, from about 0.7 to about 1.5 moles of benzenesulfonic acid are reacted with one mole of (1S,5S)-3-(5,6-dichloropyridin-3-yl)-3,6-diazabicyclo[3.2.0]heptane. Preferably about 1.1 moles of benzenesulfonic acid are used. The benzenesulfonic acid can be dissolved in any solvent suitable for dissolving (1S,5S)-3-(5,6-dichloropyridin-3-yl)-3,6-diazabicyclo[3.2.0]heptane. The solvent can be the same or different from the solvent used to dissolve the (1S,5S)-3-(5,6-dichloropyridin-3-yl)-3,6-diazabicyclo[3.2.0]heptane, but preferably the solvent systems are miscible.

Seed crystals of (1S,5S)-3-(5,6-dichloropyridin-3-yl)-3,6-diazabicyclo[3.2.0]heptane benzenesulfonate can be added to the reaction mixture or slurried with the benezenesulfonic acid solution to facilitate preparation of the (1S,5S)-3-(5,6-dichloropyridin-3-yl)-3,6-diazabicyclo[3.2.0]heptane benzenesulfonate salt. Preferably, the benzenesulfonic acid solution, with or without seed crystals of (1S,5S)-3-(5,6-dichloropyridin-3-yl)-3,6-diazabicyclo[3.2.0]heptane benzenesulfonate is added to the (1S,5S)-3-(5,6-dichloropyridin-3-yl)-3,6-diazabicyclo[3.2.0]heptane slowly to allow for the crystallization.

The process for preparing the (1S,5S)-3-(5,6-dichloropyridin-3-yl)-3,6-diazabicyclo[3.2.0]heptane benzenesulfonate salt can be better understood in connection with the following Examples, which are intended as a illustration of the compounds and methods of the invention and are not intended to limit the scope of the invention, which is defined by the appended claims.

EXAMPLES

Example 1

(1S,5S)-3-(5,6-dichloropyridin-3-yl)-3,6-diazabicyclo[3.2.0]heptane Benzenesulfonate (1S,5S)-3-(5,6-Dichloropyridin-3-yl)-3,6-diazabicyclo[3.2.0]heptane (500 mg) in 1-propanol (10 mL) was filtered through a 0.2-micron syringe filter, stirred at room temperature, and treated with a solution of benzenesulfonic acid (324 mg) in 1-propanol (2 mL). After approximately 1 minute, solids started to precipitate. The resulting slurry was stirred at room temperature for 30 minutes and filtered. The wetcake was washed with 1-propanol (1 mL) and dried overnight in a vacuum oven at 50° C. to provide the title compound as a white solid (622 mg). $^1$H NMR (DMSO, 400 MHZ) δ 2.98 (dd, J=10, 6 Hz, 1H), 3.10 (dd, J=13, 5 Hz, 1H), 3.38 (m, 1H), 3.56 (dd, J=11, 5 Hz, 1H), 3.89 (d, J=11 Hz, 1H), 4.06-4.12 (m, 1H), 4.94 (m, 1H), 7.30 (m, 3H), 7.53 (d, J=3 Hz, 1H), 7.58 (m, 2H), 7.95 (d, J=3 Hz, 1H), 8.78 (br, 1H).

Example 2

(1S,5S)-3-(5,6-dichloropyridin-3-yl)-3,6-diazabicyclo[3.2.0]heptane Benzenesulfonate Tert-butyl (1R,5S)-3-(5,6-dichloropyridin-3-yl)-3,6-diazabicyclo[3.2.0]heptane-6-carboxylate (642 mg) in 1-propanol (8 mL) was treated with benzenesulfonic acid (516 mg) and heated at 75° C. with stirring for 2 hours. The reaction mixture was cooled to room temperature, filtered, and the wetcake was dried in a vacuum oven at 50° C. to provide 292 mg of the title compound. $^1$H NMR (DMSO, 400 MHZ) δ 2.99 (dd, J=10, 6 Hz, 1H), 3.09 (dd, J=12.5 Hz, 1H), 3.39 (m, 1H), 3.56 (m, 1H), 3.89 (d, J=11 Hz, 1H), 4.05-4.11 (m, 1H), 4.94 (m, 1H), 7.29 (m, 3H), 7.55 (d, J=3 Hz, 1H), 7.58 (m, 2H), 7.97 (d, J=3 Hz, 1H), 8.80 (br, 1H).

SS NMR Data

| Frequency ppm | Intensity |
| --- | --- |
| 213.9 | 41.9 |
| 202.2 | 29.0 |
| 198.3 | 41.9 |
| 195.1 | 38.4 |
| 144.3 | 240 |
| 135.0 | 115.1 |
| 132.5 | 139.2 |
| 128.6 | 191.6 |
| 125.3 | 202.0 |
| 74.7 | 33.2 |
| 64.5 | 116.4 |
| 59.2 | 38.8 |
| 50.3 | 123.7 |
| 36.5 | 103.3 |

Example 3

(1S,5S)-3-(5,6-dichloropyridin-3-yl)-3,6-diazabicyclo[3.2.0]heptane Benzenesulfonate Amorphous (1S,5S)-3-(5,6-Dichloropyridin-3-yl)-3,6-diazabicyclo[3.2.0]heptane benzenesulfonate (3.0 g) was dissolved in water (200 mL) and 30 mL of this solution was filtered through a 0.45-micron syringe filter. The filtrate was lyophilized to provide the title compound as a white solid (450 mg). No birefringence was observed under a microscope. Upon isolation of the material, it was kept in a dry environment. Alternatively, dissolve approx 0.5 g of the besylate salt in approx 50 mL of water. The mixture was stirred until completely dissolved. The solution was filtered through a 0.2 μM filter. The solution was lyophilized and transferred to a dry atmosphere immediately upon completion of the lyophilization.

Example 4

(1S,5S)-3-(5,6-dichloropyridin-3-yl)-3,6-diazabicyclo[3.2.0]heptane Benzenesulfonate

Example 4A

Benzyl 2,2-dimethoxyethylcarbamate

N-(Benzyloxycarbonyloxy)succinimide (74.5 Kg) was charged to a 200-gallon reactor, followed by toluene (235.1 Kg). The mixture was stirred for 15 minutes and cooled to 5° C. A solution of aminoacetaldehyde dimethylacetal (30 Kg) and triethylamine (28.9 Kg) in toluene (26.1 Kg) was charged slowly to the reactor over a 1 hour period while maintaining the internal temperature below 30° C. The mixture was stirred at 20° C. until there remained no more than 1.0% CbzOSu, as determined by HPLC. Water (150 Kg) was charged to the reactor and the contents of the reactor were stirred for 15 minutes. The layers were separated and the organic layer was washed with 5% ammonium chloride (2×151 Kg) followed by a water wash (150 Kg). The product was taken onto the next step as a solution, without isolation.

Example 4B

Benzyl allyl(2,2-dimethoxyethyl)carbamate

The solution of Example 4A in toluene (343 Kg) was charged to a 200-gallon reactor followed by addition of allyl bromide (41.5 Kg) and methyltributylammonium chloride (8.3 Kg). The mixture was stirred for 15 minutes, cooled to 16° C., and treated with 50% NaOH solution (296.9 Kg) slowly over 1 hour while maintaining the internal temperature below 30° C. The mixture was stirred at room temperature until there remained no more than 1.0% 1, as determined by HPLC. The mixture was allowed to settle and the layers were separated. The organic layer was washed with phosphate buffer solution made of 10 mM $KH_2PO_4$ and 10 mM $K_2HPO_4$ (2×260 Kg), followed by a water wash (256 Kg).

Example 4C

Benzyl allyl[2-(hydroxyimino)ethyl]carbamate (3)

The solution of Example 4B (364.6 kg) was charged to a 200-gallon glass reactor and the toluene was removed by distillation performed under vacuum and at an internal temperature of below 70° C. The contents of the reactor were cooled to 23° C. and formic acid (172 Kg) was added followed by water (15.1 Kg). The contents of the reactor were stirred at room temperature until there was less than 1% of starting material remaining, as determined by GC. The contents of the reactor were cooled to 5° C. and 50% $NH_2OH$ aqueous solution (34.5 Kg) was charged slowly to the reactor over 45 minutes. The contents of the reactor were stirred at room temperature until starting material was consumed as determined by GC. Water (292 Kg) was charged to the reactor, followed by addition of n-pentanol (148 Kg). The contents of the reactor were stirred for 15 minutes. The layers were separated and the bottom aqueous layer was extracted again with n-pentanol (148 kg). The n-pentanol layers were combined and cooled to 5° C. The pH of the n-pentanol layer was adjusted to 8.5 with 25% NaOH solution (244 Kg), maintaining the internal temperature below 35° C. The layers were separated, and the n-pentanol layer was washed with 25% NaCl solution (262 Kg). The organic layer was collected and vacuum distilled at a temperature less than 85° C. The product was not isolated and was taken on to the next step as a solution.

Example 4D

Benzyl(cis)-2,2-dimethylhexahydropyrrolo[3,4-d][1,3]oxazine-6(4H)-carboxylate

A solution of Example 4C in n-pentanol (25.2 wt %) was charged to a 200-gallon glass-lined reactor, equipped with a mechanical agitator, condenser, temperature probe and nitrogen inlet. Each drum was rinsed with 10±5 Kg of pentanol. n-Pentanol (363 Kg) was charged to the reactor and the contents of the reactor was heated at 133° C.-135° C. for 13 hours. The contents of the reactor were then cooled to below 50° C. The reaction was cooled to room temperature and then transferred to tared poly-lined drums. The product was not isolated, and was taken on to the next step as a solution.

Example 4E

Benzyl(cis)-3-amino-4-(hydroxymethyl)-1-pyrrolidinecarboxylate

Raney Nickel (6.2 Kg, 25 wt %) was charged to a reactor that had been pressure purged with nitrogen three times. To a second reactor was charged ethanol (30 Kg) and then the reactor was pressure purged with nitrogen 3 times. The contents of the reactor were transferred to the first reactor containing the Raney Nickel. The reactor containing the mixture was pressure purge 3 times with nitrogen. The agitator of the first reactor was started, being careful not to splash the solution. The n-pentanol (298.7 Kg) containing benzyl(cis)-2,2-dimethylhexahydropyrrolo[3,4-d][1,3]oxazine-6(4H)-carboxylate (24.9 Kg) was charged to the second reactor and each drum was rinsed with 5 Kg of ethanol. The reactor was pressure purged 3 times with nitrogen. The n-pentanol solution of benzyl(cis)-2,2-dimethylhexahydropyrrolo[3,4-d][1,3]oxazine-6(4H)-carboxylate was transferred to the reactor containing the catalyst, and the reactor was pressure purged 3 times with nitrogen. Ethanol (21 Kg) was then added, and the reactor pressure purged 3 times with nitrogen. The internal temperature of the reactor was adjusted to 25±5° C. and pressure purged with hydrogen 3 times. The solution was hydrogenated at about 40-60 psig for 4 hours while maintaining an internal temperature of 25±15° C. Upon completion of the reaction, the contents of the reactor were filtered through filter aid to remove the catalyst and the solution was collected in poly-lined drums. The product was not isolated, and was taken on to the next step as a solution.

Example 4F

Benzyl(cis)-3-amino-4-(hydroxymethyl)-1-pyrrolidinecarboxylate (S)-Mandelate

A solution of Example 4E in n-pentanol/ethanol was charged to a glass-lined reactor, equipped with a mechanical agitator, condenser, temperature probe and nitrogen inlet. The contents of the reactor were distilled under vacuum with a jacket temperature of NMT 85° C. to a volume of 400 L. The internal temperature was then adjusted to 25° C. n-Pentanol (166.2 Kg) was charged to the reactor, followed by (S)-mandelic acid (17.0 Kg). The internal temperature of the reactor was adjusted to 75° C. The internal temperature was then adjusted to 60° C., at which point seed crystals (250 g) were added to the reactor. The contents of the reactor were stirred at an internal temperature of 60±5° C. for not less than 3 hours. The internal temperature of the reactor was lowered to 25° C. at a rate of 5° C. per hour, and then the contents of the reactor were stirred at 25° C. for not less than 6 hours. The contents of the reactor were filtered and the wetcake was washed with n-pentanol (50 Kg). After the wetcake was blown dry with nitrogen for at least 4 hours, the obtained solid was dried for at least 24 hours in a hastelloy tray dryer under vacuum at 55° C. with a nitrogen bleed to provide 27.7 Kg (38%) of the title compound with >99% purity and 96% diastereomeric excess.

Example 4G

Benzyl (3S,4S)-3-[(tert-butoxycarbonyl)amino]-4-(hydroxymethyl)-1-pyrrolidinecarboxylate To a glass-lined reactor was charged Example 4F (13.3 Kg). The reactor was evacuated and purged three times with nitrogen. Ethyl acetate (89.9 Kg) was charged, and the internal temperature adjusted to 25° C. To this slurry was charged a 50 wt % solution of aqueous potassium carbonate (73 Kg). To the stirred suspension was charged a solution of di-tert-butyldicarbonate (9.4 Kg) in ethyl acetate (44.2 Kg). The reaction mixture was quenched with N,N-dimethylethylenediamine (0.55 Kg), followed by the addition of ethyl acetate (85.8 Kg) and water (66 Kg). After separating the layers, the organic layer was washed with a solution of potassium phosphate buffer (28.4 kg). The buffer solution was made using 13.3 g potassium phosphate monobasic and 50.8 g potassium phosphate dibasic per kilogram of water. The wash was repeated until the pH of the aqueous solution after the wash was less than 8.0. The organic layer was washed with a 20 wt % solution of sodium chloride (75 kg). The ethyl acetate solution was distilled under vacuum at jacket temperature of not more than 50° C., maintaining the internal volume at approximately 100 liters. Distillation was continued, maintaining the same volume until 200±10 Kg of ethylene glycol dimethyl ether had been charged and distilled. The product slurry was used immediately in the next step.

Example 4H

Benzyl(3S,4S)-3-[(tert-butoxycarbonyl)amino]-4-{[(methylsulfonyl)oxy]methyl}-1-pyrrolidinecarboxylate To the slurry of Example 4G in ethylene glycol dimethyl ether (DME) was charged triethylamine (7.5 kg). The temperature was adjusted to −10° C., maintaining the internal temperature at not more than 5° C., and methane sulfonyl chloride (5.8 kg) was slowly added. Stirring was continued, and the reaction sampled after 30 minutes for completion. Once the reaction was judged to be complete, the next step was immediately performed.

Example 4I

Benzyl (3S,4S)-3-(amino)-4-{[chloro methyl}-1-pyrrolidinecarboxylate hydrochloride A solution of 6M HCl (60 Kg) was charged to a glass-lined reactor, and the internal temperature adjusted to 10° C. The solution of Example 4H in DME was added to the reactor, maintaining the internal temperature below 20° C. DME (20 Kg) was used to rinse out any residual solution of Example 4H. The reaction mixture was then heated to an internal temperature of 40° C. and mixed for not less than 2 hours. The reaction mixture was stirred at 40° C. until complete. The product was used immediately in the next step.

Example 4J

Benzyl (1S,5S)-3,6-diazabicyclo[3.2.0]heptane-3-carboxylate 4-methylbenzenesulfonate While maintaining the internal temperature at not more than 20° C., the pH of the acidic solution of Example 4I was adjusted to 5.5 using 50 wt % sodium hydroxide solution (45.3 Kg). The remaining DME was distilled off, using a jacket temperature of 45° C., until the volume of the batch was approximately 150 L. At this stage, ethanol (30 Kg) was added, and the pH was adjusted to 12.4, using 50 wt % sodium hydroxide (10.1 Kg), while maintaining the internal temperature at less than 60° C. Following the pH-adjustment, the internal temperature was adjusted to 55° C. and the reaction was stirred at 55° C. until complete. More 50 wt % sodium hydroxide (2.1 Kg) was added during the reaction to maintain the pH between 12-13. The reaction mixture was cooled to 30° C., and then vacuum distilled with an internal temperature of 50° C., to a volume of approximately 150 liters. Water (60 Kg) and isopropyl acetate (96 Kg) were then added, and the pH was adjusted to 12-13 with 50 wt % sodium hydroxide (7.5 Kg). The layers were separated, and the aqueous layer extracted with more isopropyl acetate (50 Kg). The combined organic layers were then washed with a 20 wt % solution of sodium chloride (67.5 Kg). The isopropyl acetate solution was vacuum distilled, with the jacket temperature below 50° C., to a volume of approximately 50 liters. Isopropyl acetate (110 Kg) was added and distillation continued until it was determined that the water content was low enough. p-Toluenesulfonic acid (5.3 Kg; 1.1 equivalents) was charged to a reactor, followed by ethyl acetate (26.1 Kg). The internal temperature was adjusted to 50° C. The solution of free-base in isopropyl acetate was then filtered into the p-TsOH solution, followed by the addition of seed crystals (120 g). The reaction mixture was stirred at 50° C. for 30 minutes and cooled to 20° C. at 10° C. per hour. The slurry was filtered and the reactor walls and the wet cake were then rinsed with isopropyl acetate (40 Kg). The wetcake was charged back to the reactor followed by ethyl acetate (91 Kg). The resultant slurry was stirred at 50° C. for 1 hour, cooled to room temperature, filtered, and the obtained solid dried in a vacuum oven at 50° C. until dry to provide 10.1 Kg of the title compound corresponding to a 76% yield from Example 4F. The material was 98% pure as determined by HPLC.

Example 4K

3-Benzyl, 6-tert-butyl-(1R,5S)-3,6-diazabicyclo[3.2.0]heptane-3,6-dicarboxylate

Toluene (125.5 Kg) and Example 4J (18.0 Kg) were charged to a glass-lined reactor, equipped with a mechanical agitator, condenser, temperature probe, and nitrogen inlet. The mixture was stirred for not less than 10 minutes and treated with 15 wt % aqueous potassium carbonate solution (330 Kg). The internal temperature was adjusted to 20° C. maintaining the internal temperature at less than 30° C. A cold (15° C.) solution of di-tert-butyldicarbonate (12.1 Kg) in toluene (25 Kg) was added followed by a toluene rinse (10 Kg). After the addition was complete, the temperature was adjusted to 25° C. and the mixture was stirred until reaction was complete. The layers were separated and the organic layer was quenched with N,N-dimethylethylenediamine (1.3 Kg). The mixture was washed four times with a 5 wt % solution of aqueous ammonium chloride (200 Kg). The organic layer was then washed with a 10 wt % solution of aqueous sodium chloride (200 Kg). The product was not isolated, but used as a solution in the next step.

Example 4L tert-Butyl (1R,5S)-3,6-diazabicyclo[3.2.0]heptane-6-carboxylate

5% Palladium on carbon (2.9 Kg) was charged to a reactor that had been pressure purged three times with nitrogen. Following the catalyst charge, the reactor was pressure purged again with nitrogen. The solution of Example 4K in toluene (200.4 Kg) was charged to a second reactor, followed by an ethanol rinse (5 Kg per drum). The reactor was then pressure purged three times with nitrogen. More ethanol (95.2 Kg) was charged, followed by a nitrogen pressure purge. This mixture was then transferred to the reactor containing the catalyst. The reactor was pressure purged three times with nitrogen and the internal temperature adjusted to 25° C. It was then pressure purged three times with hydrogen and the solution was hydrogenated for 2 hours at 40 psig maintaining the internal temperature at 25° C. The reactor was pressure purged three times with hydrogen and the reaction was hydrogenated for not less than 1 hour at 40 psig maintaining the internal temperature at 25° C. The reaction was filtered with a pressure filter set up with 2 filter papers, filter aid (5 Kg) and two back-up filters, a six-pack and a cuno in-line filter. The solution assay was vacuum distilled with a jacket temperature of not more than 60° C. to a volume of approximately 60 liters. Toluene (332.5 Kg) was added and the distillation continued until the solution had acceptable levels of ethanol and water. The solution was transferred to a tared pressure canister providing 23.8 Kg solution corresponding to 6.85 Kg (77%) of the title compound.

Example 4M tert-butyl (1R,5S)-3-(5,6-dichloropyridin-3-yl)-3,6-diazabicyclo[3.2.0]heptane-6-carboxylate A 30-gallon reactor was charged 3-bromo-5,6-dichloropyridine (4.7 Kg), xantphos (499 g), and palladium acetate (79 g). The reactor was pressure purged three times. Tert-butyl (1R,5S)-3,6-diazabicyclo[3.2.0]heptane-6-carboxylate (3.43 Kg) in toluene (21.4 Kg) was filtered into the reactor. All the lines were then rinsed with toluene (3.0 Kg) and the contents of the reactor were pressure purged three times with nitrogen and then heated to 75° C.

A solution of sodium tert-butoxide (2.4 Kg) in DME (9.0 Kg) was filtered into the reactor addition funnel followed by a DME (1.3 Kg) rinse. The sodium tert-butoxide/DME solution was slowly added to the contents of the reactor while maintaining the internal temperature at not more than 90° C. Following the addition, the contents of the reactor were held at 85° C. for 5 minutes and then cooled to room temperature. The reaction was sampled until judged to be complete. The mixture was quenched with water (150 g), stirred for 15 minutes, and filtered through a pad of filteraid (1.0 Kg). The filteraid was rinsed with toluene (18 Kg). The toluene filtrate was washed with ammonium hydroxide (36 Kg) for more than 12 hours. A solution of 20% aqueous sodium chloride (43 Kg) was added and the layers were separated. The toluene solution was washed with 20% sodium chloride (28 Kg), followed by two 10% ammonium chloride (40 Kg) washes and a final 10% sodium chloride (25 Kg) wash. The product was not isolated, but was taken into the next step as a toluene solution.

Example 4N (1S,5S)-3-(5,6-dichloropyridin-3-yl)-3,6-diazabicyclo[3.2.0]heptane Benzenesulfonate A 30-gallon reactor was charged with a solution of tert-butyl (1R,5S)-3-(5,6-dichloropyridin-3-yl)-3,6-diazabicyclo[3.2.0]heptane-6-carboxylate (11.2 Kg) in toluene (77.1 Kg). The mixture was distilled to a volume of approximately 12 L, treated with n-propanol (45 Kg), filtered into a tared drum, and the reactor was rinsed with n-propanol (5 Kg). Deloxan™ THP resin (5 Kg) was charged to a filter pot and washed with n-propanol until water was removed from the resin. The resin was charged to a pressure canister, followed by the solution of tert-butyl (1R,5S)-3-(5,6-dichloropyridin-3-yl)-3,6-diazabicyclo[3.2.0]heptane-6-carboxylate in n-propanol. After stirring for at least 12 hours at room temperature, the resin was filtered off and the residue was washed with n-propanol (10 Kg). The solution was charged to a 30-gallon reactor, warmed to 40° C., and treated with a solution of benzenesulfonic acid (6.12 Kg) in n-propanol (9.8 Kg) that was filtered into the reactor. The resulting solution was seeded with product seed crystals (100 g), stirred at 40° C. for at least 12 hours, the temperature was increased to 60° C., and the mixture was stirred at 60° C. for about 4 hours. The reaction mixture was slowly cooled to room temperature, at a rate of 10° C./hour. The mixture was stirred at room temperature for 12 hours, filtered, and the wetcake washed with n-propanol (20 Kg). The obtained solid was dried under vacuum in a tumble dryer at 55° C. to provide 9.55 Kg (92%) of the title compound.

Example 5

(1S,5S)-3-(5,6-Dichloro-pyridin-3-yl)-3,6-diazabicyclo[3.2.0]heptane (1S,5S)-3-(5,6-dichloropyridin-3-yl)-3,6-diazabicyclo[3.2.0]heptane benzenesulfonate (250 g) was suspended in methylene chloride (1000 mL). 20% aqueous potassium hydroxide (700 mL) was added and, after mixing and settling, the layers were separated. The organic layer was washed two more times with 700 mL 20% aqueous potassium hydroxide, followed by a 700 mL water wash. The combined organic layers were dried over sodium sulfate and then concentrated to an oil. The residue was dissolved in isopropyl acetate (1000 mL) and concentrated to a solid. The residue was then suspended in isopropyl acetate (1000 mL) and heated to 80° C. to dissolve everything. Insolubles were removed by filtration. The solution was cooled to room temperature, with rapid stirring. The resulting slurry was concentrated further by distillation of approximately 250 mL isopropyl acetate. After cooling in the refrigerator for 3 hours (~5° C.), the product was isolated by filtration. The wetcake was washed with isopropyl acetate and then dried in a vacuum oven at 50° C. An off-white solid was obtained (109.6 g).

Example 6

(1S,5S)-3-(5,6-dichloropyridin-3-yl)-3,6-diaza-bicyclo[3.2.0]heptane

Example 6A (1S,5S)-3-(5,6-Dichloro-pyridin-3-yl)-3,6-diaza-bicyclo[3.2.0]heptane (1S,5S)-3-(5,6-Dichloro-pyridin-3-yl)-3,6-diaza-bicyclo[3.2.0]heptane salt (10.0 g) was partitioned between methylene chloride (200 mL) and 20% aqueous potassium hydroxide (150 mL). The layers were separated, and the organic layer was washed with more 20% aqueous potassium hydroxide (2×150 mL). The organic layer was then washed with saturated brine solution (100 mL). This was concentrated to an oily solid, and then dissolved up in isopropyl acetate. Upon concentration by distillation to ~50 mL, solids started to crystallize. More isopropyl acetate (200 mL) was added and this was concentrated to ~25 mL. After cooling in an ice bath, the resulting solids were filtered and the wetcake was washed with isopropyl acetate. The product was dried in the vacuum oven at 50° C. to give a solid. $^1$H NMR (CDCl$_3$, 400 MHZ) δ 3.04 (dd, J=11.8 Hz, 1H), 3.15 (dd, J=10.7 Hz, 1H), 3.30-3.38 (m, 2H), 3.6 (d, J=11 Hz, 1H), 3.88 (d, J=10 Hz, 1H), 3.91 (t, J=8 Hz, 1H), 4.60 (m, 1H), 7.07 (d, J=3 Hz, 1H), 7.75 (d, J=3 Hz, 1H).

Example 6B

3-Chloro-2-hydroxy-5-nitropyridine

Concentrated hydrochloric acid (239 g) was added to 2-hydroxy-5-nitropyridine (40.0 g). The resulting slurry was heated to 53° C., and stirred until all the solids dissolved. To this was slowly added a solution of potassium chlorate (14.0 g) in water (250 g), while maintaining the temperature between 55° C. and 59° C. The resulting mixture was stirred at 58-62° C. for about 1 hour. The reaction was then cooled to room temperature, stirred for 12 hours and then filtered. After washing the wet cake with water, the product was dried in a vacuum oven. $^1$H NMR (400 MHz/DMSO-d6) δ 8.64 (d, J=2.9 Hz, 1H), 8.35 (d, J=2.9 Hz, 1H)

Example 6C 2,3-Dichloro-5-nitropyridine (Compound 6C)

A mixture of 3-chloro-2-hydroxy-5-nitropyridine (36.0 g), acetonitrile (72 mL), and phosphorus oxychloride (37.5 g) was heated to 80° C. The reaction was then stirred at this temperature for about 15 hours. After cooling the reaction to 40° C., water (27 g) was added, while maintaining the temperature below 70° C. The temperature was adjusted to 45° C., and then more water (189 g) was added slowly. The reaction was then cooled to 23° C., stirred for at least 12 hours, and then filtered. After washing the wet cake with water, the product was dried in a vacuum oven. $^1$H NMR (400 MHz/CDCl$_3$) δ 9.10 (d, J=2.5 Hz, 1H), 8.56 (d, J=2.4 Hz, 1H)

Example 6D (5,6-Dichloro-pyridin-3-yl)-(2,2-dimethoxy-ethyl)-amine

To a Parr bottle was charged Raney Nickel (10.1 g), water (40.0 g), tetrahydrofuran (166.3 g), ethanol (32.0 g) and acetic acid (2.5 g). A solution of 2,3-dichloro-5-nitropyridine (40.0 g) in tetrahydrofuran (40.1 g) was added to the Parr bottle in four portions and the mixture was hydrogenated at 40 psi and 35° C. for about 1 hour after each addition. The reaction mixture was cooled to room temperature, and then glyoxal-1,2-dimethyl acetal (47.2 g of 50 wt % aqueous), tetrahydrofuran (35.6 g) and water (80.4 g) were added and the mixture was hydrogenated at 40 psi and 50° C. for about 12 hours. The reaction was cooled to room temperature and then filtered through a bed of Hy-Flo. The pH of the filtrate was adjusted to 7 with 5% aqueous phosphoric acid, and then the mixture was concentrated. Isopropyl acetate (79 g) was added, this was concentrated, and then more isopropyl acetate (485 g) was added. After warming to 50° C. to dissolve the solids, the solution was washed with 5% aqueous phosphoric acid (3×215 g) and then washed with 20% aqueous sodium chloride solution (231 g). The organic solution was concentrated to about 78 mL and heptane (124 g) was added. After heating to 83° C. to dissolve everything, the solution was slowly cooled to room temperature. More heptane (124 g) was added and then the suspension was cooled to 5° C. After filtering, the wetcake was washed with cold heptane/isopropyl acetate and then dried in the vacuum oven. $^1$H NMR (400 MHz/CDCl$_3$) δ 7.71 (d, J=2.7 Hz, 1H), 7.01 (d, J=2.7 Hz, 1H), 4.53 (t, J=5.2 Hz, 1H), 4.05 (s, br, 1H), 3.42 (s, 6H), 3.22 (d, J=5.21 Hz, 2H).

Example 6E

Allyl-(5,6-dichloro-pyridin-3-yl)-(2,2-dimethoxy-ethyl)-amine (Compound 6E)

To a mixture of (5,6-dichloro-pyridin-3-yl)-(2,2-dimethoxy-ethyl)-amine (190 g), allyl bromide (137.4 g), and methyl tributyl ammonium chloride (23.8 g) in methyl tert-butyl ether (1140 mL) was added 50% aqueous sodium hydroxide (665 mL). This was then stirred at 25-35° C. for about 24 hours. Then water (375 g) and methyl tert-butyl ether (280 g) were added and then the layers were separated. The organic layer was washed with 10 mM potassium phosphate dibasic/10 mM potassium phosphate monobasic aqueous solution (3×1000 mL), and then washed with 20% aqueous sodium chloride (1000 mL). The solution was concentrated to a small volume and then dissolved back up in tetrahydrofuran (1720 g). $^1$H NMR (400 MHz/CDCl$_3$) δ 7.79 (d, J=3.02 Hz, 1H), 7.10 (d, J=3.02 Hz, 1H), 5.81-5.70 (m, 1H), 5.20 (ddd, J=1.78, 3.02 10.43 Hz, 1H), 5.09 (ddd, J=1.9, 3.2, 17.1 Hz, 1H). 4.48 (t, J=5.1 Hz, 1H), 4.00-3.95 (m, 2H), 3.43 (d, J=5.1, 2H), 3.41 (s, 6H).

Example 6F 2-(S)-Hydroxyamino-2-phenyl-ethanol

A solution of(S)-phenylglycinol (15 g) and p-anisaldehyde (16.4 g) in methyl tert-butyl ether (150 mL) was heated to reflux, with a Dean-Stark trap attached, for about 3 hours. Tetrahydrofuran (60 mL) was added and the mixture cooled to 0° C. To this was added a solution of m-chloroperoxybenzoic acid (29.8 g) in methyl tert-butyl ether (80 mL), maintaining the temperature below 5° C. The mixture was stirred at 0° C. for about 3 hours. Then the reaction mixture was washed with 10% aqueous potassium carbonate (3×75 mL). The resulting organic layer was concentrated to a smaller volume. To this was added a solution of hydroxylamine hydrochloride (15.3 g) in methanol (19 mL) and water (27 mL), and the reaction was stirred at room temperature for about 3 hours. Heptane (30 mL) and water (30 mL) were added. The layers were separated, and the aqueous layer was washed with methyl tert-butyl ether (3×30 mL). The methanol was removed by vacuum distillation, and then methyl tert-butyl ether (75 ml) was added. After adjusting the pH to 7 with solid potassium carbonate, sodium chloride was added and the layers separated. The aqueous layer was further extracted with methyl tert-butyl ether (2×75 mL). The combined methyl tert-butyl ether extracts were filtered, concentrated to a small volume, and then heptane (70 mL) was added. The resulting slurry was stirred at room temperature for about 1 hour and then cooled to 0° C. After stirring for 1 hour, the mixture is filtered and the wetcake washed with heptane (20 mL). The wetcake was then dissolved in dichloromethane (100 mL) for use in the next step. $^1$H NMR (400 MHz, CDCl$_3$) δ 3.83-3.91 (2H, m), 4.12 (1H, dd, J=6.9, 4.8 Hz), 4.84 (3H, br s), 7.27-7.36 (5H, m). $^{13}$C NMR (100 MHz, CDCl$_3$) δ 63.8, 67.7, 127.5, 127.9, 128.4, 137.5.

Example 6G

[Allyl-(5,6-dichloro-pyridin-3-yl)-amino]-acetaldehyde (Compound 6G)

A solution of allyl-(5,6-dichloro-pyridin-3-yl)-(2,2-dimethoxy-ethyl)-amine (57.2 g) in tetrahydrofuran (443 g) was cooled to 10° C. A solution of concentrated hydrochloric acid (136 g) in water (114 g) was slowly added, maintaining the temperature below 20° C. The reaction was then stirred at 15° C. for about 4 hours. Then dichloromethane (570 g) and water (430 g) were added and the layers separated. The organic layer was washed with 5% aqueous sodium bicarbonate (453 g), and then washed twice with water (430 g). The organic layer was concentrated and the residue dissolved in dichloromethane (580 g).

Example 6H (3S,4S)-2-[5-(5,6-Dichloro-pyridin-3-yl)-hexahydro-pyrrolo[3,4-c]isoxazol-1-yl]-2-(2'S)-phenyl-ethanol (Compound 6H)

2-(S)-Hydroxyamino-2-phenyl-ethanol (13.8 g) was dissolved in dichloromethane (180 mL). To this was added magnesium bromide (15.9 g) and isopropyl alcohol (5.2 g). This mixture was stirred for 30 minutes, and then [allyl-(5,6-dichloro-pyridin-3-yl)-amino]-acetaldehyde (18.4 g) in dichloromethane (223 g) was added slowly. The reaction was stirred at 30° C. for about 5 hours. To the reaction was added 10% aqueous ammonium acetate (200 mL). The layers were separated and then the organic layer was washed with water (200 mL). The solution was concentrated to an oil, dissolved up in isopropyl alcohol (200 mL) and concentrated to an oil. The resulting oil was dissolved in isopropyl alcohol (100 mL) and heated to 80° C. to dissolve all the solids. The solution was cooled slowly to room temperature at which point heptane (100 mL) was added and the mixture heated to 60° C. Upon cooling to room temperature, the mixture was filtered. After washing the wet cake with isopropyl alcohol, the product was dried in a vacuum oven.
$^1$H NMR (400 MHz/CDCl$_3$) δ 7.51 (d, J=2.7 Hz, 1H), 7.33 (m, 5H), 6.83 (d, J=2.6 Hz, 1H), 4.11 (m, 1H), 3.80-3.91 (m, 3H), 3.74 (dd, J=3.5, 11.6 Hz, 1H), 3.32-3.40 (m, 3H), 3.12 (m, 2H).

Example 6I (3S,4S)-5-(5,6-Dichloro-pyridin-3-yl)-hexahydro-pyrrolo[3,4-c]isoxazole (Compound 6I)

A solution of (3S,4S)-2-[5-(5,6-dichloro-pyridin-3-yl)-hexahydro-pyrrolo[3,4-c]isoxazol-1-yl]-2-(2'S)-phenyl-ethanol (30 g) and triethylamine (11.2 g) in tetrahydrofuran (222 g) was cooled to 0° C. Methanesulfonyl chloride (11.1 g) was slowly added and then the mixture was stirred at 5° C. for about 1 hour. A solution of sodium tert-butoxide (21.1 g) in tetrahydrofuran (133 g) was added and then the mixture stirred at room temperature for about 2 hours. After adding water (44.5 g), the pH was adjusted to 7.9 with 3M aqueous hydrochloric acid (31 g). The solution was concentrated to about 90 mL, water (100 mL was added and then the pH was adjusted to 0.8 with 3M aqueous hydrochloric acid (28 g). The aqueous solution was washed with toluene/heptane (1:1; 2×150 ml). Isopropyl alcohol (150 mL) was added and then the pH was adjusted to 4.4 with 10% aqueous potassium phosphate (55 g). The mixture was heated to 78° C. and then slowly cooled to 45° C. Water (325 g) was slowly added and then the product was filtered. The wetcake was slurried in isopropyl alcohol (75 mL) and water (68 mL), and then heated to 80° C. The resulting solution was cooled slowly to 35° C., at which point water (232 mL) was slowly added. After stirring at room temperature for about 5 hours, the product was filtered, washed with isopropyl alcohol/water (1:4; 30 mL) and then dried in the vacuum oven. $^1$H NMR (400 MHz/CDCl$_3$) δ 7.68 (d, J=2.9 Hz, 1H), 6.99 (d, J=2.7 Hz, 1H), 4.32 (dt, J=3.6, 11.9 Hz, 1H), 3.99-3.83 (m, 2H), 3.61-3.52 (m, 2H). 3.39 (m, 1H), 3.34 (dd, J=3.7, 10.43 Hz, 1H), 3.29 (dd, J=3.8, 9.7 Hz, 1H).

Example 6J (3S,4S)-[4-Amino-1-(5,6-dichloro-pyridin-3-yl)-pyrrolidin-3-yl]-methanol (Compound 6J)

Raney Nickel (7.5 g) was charged to a Parr reactor. To this was added a solution of (3S,4S)-5-(5,6-dichloro-pyridin-3-yl)-hexahydro-pyrrolo[3,4-c]isoxazole (50 g) in tetrahydrofuran (625 mL), ethanol (625 mL) and water (2 mL). The mixture was hydrogenated at 40 psi and room temperature for about 3 hours. The reaction mixture was filtered through a bed of HyFlo and then concentrated to about 100 mL. Isopropyl alcohol (150 mL) was added and this was concentrated to about 100 mL. More isopropyl alcohol (100 mL) was added and then the mixture was heated to 80° C. Heptane (250 mL)

was added, then the mixture was cooled to room temperature and filtered. After washing the wet cake with heptane, the product was dried in a vacuum oven. $^1$H NMR (400 MHz/ DMSO-d6) δ 7.61 (d, J=2.8 Hz, 1H), 7.10 (d, J=2.8 Hz, 1H), 3.63 (m, 2H), 3.50 (m, 1H), 3.43 (m, 1H), 3.30 (m, 2H), 3.13 (t, J=9 Hz, 1H), 3.05 (dd, J=3, 10 Hz, 1H).

Example 6K (1S,5S)-3-(5,6-dichloropyridin-3-yl)-3,6-diaza-bicyclo[3.2.0]heptane (Compound 6K)

(3S,4S)-[4-Amino-1-(5,6-dichloro-pyridin-3-yl)-pyrrolidin-3-yl]-methanol (10 g) was suspended in 1,2-dimethoxyethane (100 mL) and N-methylpyrrolidinone (15 mL). The mixture was heated to 50° C. and then a solution of thionyl chloride (7.9 g) in 1,2-dimethoxyethane (35 mL) was slowly added, while maintaining the temperature below 60° C. The reaction mixture was stirred at 50° C. for about 3 hours and then cooled to room temperature. After adding water (100 mL), the 1,1-dimethoxyethane was removed by distillation. Ethanol (100 mL) and water (100 mL) were added and the pH adjusted to 11-12 with 50% aqueous sodium hydroxide. The resulting mixture was heated at 60° C. for at least 12 hours and then cooled to room temperature. After filtering through a bed of Hy-Flo, the ethanol was removed by vacuum distillation. The pH was adjusted to >12 with 50% aqueous sodium hydroxide and then extracted with isopropyl acetate (2×80 mL). The combined organic extracts were concentrated, and then suspended in isopropyl acetate (~50 mL). After heating to 80° C., the solution was cooled to room temperature while stirring rapidly. The suspension was cooled to 0° C., filtered, washed with isopropyl acetate and dried in the vacuum oven. $^1$H NMR (MeOH-d$_4$, 300 MHz) δ 3.04 (dd, J=10.9, 4.8 Hz, 1H), 3.11 (dd, J=10.2, 6.8 Hz, 1H), 3.26 (dd, J=8.8, 4.4 Hz, 1H), 3.38 (m, 1H), 3.73 (t, J=11.2 Hz, 2H), 3.84 (t, J=8.1 Hz, 1H), 4.55 (dd, J=6.8, 4.8 Hz, 1H), 7.37 (d, J=3.1 Hz, 1H), 7.84 (d, J=2.7 Hz, 1H); MS (DCI/NH$_3$) m/z 244/246/248 (M+H)$^+$.

Example 7

(1S,5S)-3-(5,6-dichloropyridin-3-yl)-3,6-diazabicyclo[3.2.0]heptane benzenesulfonate (1S,5S)-3-(5,6-Dichloropyridin-3-yl)-3,6-diazabicyclo [3.2.0]heptane (14 g) in ethanol with 5% methanol (70 g) was stirred at 25° C. A solution of benzenesulfonic acid (0.6 g) in ethanol with 5% methanol (0.6 g) was slurried with seeds of (1S,5S)-3-(5,6-dichloropyridin-3-yl)-3,6-diazabicyclo [3.2.0]heptane benzenesulfonate (0.5 g), and then added to the reactor. The slurry was held for 15 minutes, and then a solution of benzenesulfonic acid (9.3 g) in ethanol with 5% methanol (9.3 g) was added over 2 hours. The slurry was filtered and the wet cake was washed with ethanol with 5% methanol (14 g) and dried overnight in a vacuum oven at 50° C. to provide the title compound as a yellow solid (24 g).

It is to be understood that the active agent of (1S,5S)-3-(5, 6-dichloropyridin-3-yl)-3,6-diazabicyclo[3.2.0]heptane benzenesulfonate is (1S,5S)-3-(5,6-dichloropyridin-3-yl)-3,6-diazabicyclo[3.2.0]heptane and therefore the salt has utility in disease states involving cognitive deficits and can be used in combination with other pharmaceutically acceptable cognitive enhancing active compounds. As a salt of (1S,5S)-3-(5,6-dichloropyridin-3-yl)-3,6-diazabicyclo[3.2.0]heptane, it is expected that (1S,5S)-3-(5,6-dichloropyridin-3-yl)-3,6-diazabicyclo[3.2.0]heptane benzenesulfonate would demonstrate sufficient binding potency to treat cognitive deficit in a mammal, demonstrate analgesic effect, and improve alllodynia related to treatment for neuropathic pain.

(1S,5S)-3-(5,6-dichloropyridin-3-yl)-3,6-diazabicyclo [3.2.0]heptane benzenesulfonate can be used to treat pain via nicotinic acetylcholine receptors and as further described by M. Williams and S. P. Arneric, "Beyond the Tobacco Debate: dissecting out the therapeutic potential of nicotine" Exp. Opin. Invest. Drugs 5(8):1035-1045 (1996); and S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Additionally, (1S,5S)-3-(5,6-dichloropyridin-3-yl)-3,6-diazabicyclo[3.2.0]heptane benzenesulfonate is useful for ameliorating or preventing disorders affected by nicotinic acetylcholine receptors, such as Alzheimer's disease, Parkinson's disease, memory dysfunction, Tourette's syndrome, sleep disorders, attention deficit hyperactivity disorder, neurodegeneration, inflammation, neuroprotection, anxiety, depression, mania, schizophrenia, anorexia and other eating disorders, AIDS-induced dementia, epilepsy, urinary incontinence, substance abuse, smoking cessation and inflammatory bowel syndrome.

Compounds that bind to the nicotinic acetylcholine receptor can be used to treat Alzheimer's disease as described by M. Williams and S. P. Arneric, "Beyond the Tobacco Debate: dissecting out the therapeutic potential of nicotine" Exp. Opin. Invest. Drugs 5(8):1035-1045 (1996); S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); S. P. Americ, M. W. Holladay, J. P. Sullivan, "Cholinergic channel modulators as a novel therapeutic strategy for Alzheimer's disease" Exp. Opin. Invest. Drugs 5(1):79-100 (1996); J. Lindstrom, "Nicotinic Acetylchloline Receptors in Health and Disease" Molecular Neurobiology 15:193-222 (1997); and G. K. Lloyd, et al., "The potential of subtype selective neuronal nicotinic acetylcholine receptor agonists as therapeutic agents" Life Sciences 62(17/18):1601-1606 (1998).

Compounds that bind to the nicotinic acetylcholine receptor can be used to treat Parkinson's disease as described by M. Williams and S. P. Arneric, "Beyond the Tobacco Debate: dissecting out the therapeutic potential of nicotine" Exp. Opin. Invest. Drugs 5(8):1035-1045 (1996); J. Lindstrom, "Nicotinic Acetylchloline Receptors in Health and Disease" Molecular Neurobiology 15:193-222 (1997); and G. K. Lloyd, et al., "The potential of subtype selective neuronal nicotinic acetylcholine receptor agonists as therapeutic agents" Life Sciences 62(17/18): 1601-1606 (1998).

Compounds that bind to the nicotinic acetylcholine receptor can be used to treat memory dysfunction as described by M. Williams and S. P. Arneric, "Beyond the Tobacco Debate: dissecting out the therapeutic potential of nicotine" Exp. Opin. Invest. Drugs 5(8):1035-1045 (1996); S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat Tourette's syndrome as described by M. Williams and S. P. Arneric, "Beyond the Tobacco Debate:

dissecting out the therapeutic potential of nicotine" Exp. Opin. Invest. Drugs 5(8):1035-1045 (1996); S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat sleeping disorders as described by M. Williams and S. P. Americ, "Beyond the Tobacco Debate: dissecting out the therapeutic potential of nicotine" Exp. Opin. Invest. Drugs 5(8):1035-1045 (1996).

Compounds that bind to the nicotinic acetylcholine receptor can be used to treat attention deficit hyperactivity disorder as described by M. Williams and S. P. Arneric, "Beyond the Tobacco Debate: dissecting out the therapeutic potential of nicotine" Exp. Opin. Invest. Drugs 5(8):1035-1045 (1996); and S. P. Arneric, M. W. Holladay, J. P. Sullivan, "Cholinergic channel modulators as a novel therapeutic strategy for Alzheimer's disease" Exp. Opin. Invest. Drugs 5(1):79-100 (1996).

Compounds that bind to the nicotinic acetylcholine receptor can be used to treat neurodegeneration and to provide neuroprotection as described by S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and S. P. Arneric, M. W. Holladay, J. P. Sullivan, "Cholinergic channel modulators as a novel therapeutic strategy for Alzheimer's disease" Exp. Opin. Invest. Drugs 5(1):79-100 (1996).

Compounds that bind to the nicotinic acetylcholine receptor can be used to treat inflammation as described by S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and S. P. Arneric, M. W. Holladay, J. P. Sullivan, "Cholinergic channel modulators as a novel therapeutic strategy for Alzheimer's disease" Exp. Opin. Invest. Drugs 5(1):79-100 (1996).

Compounds that bind to the nicotinic acetylcholine receptor can be used to treat amyotrophic lateral sclerosis as described by M. Williams and S. P Arneric, "Beyond the Tobacco Debate: dissecting out the therapeutic potential of nicotine" Exp. Opin. Invest. Drugs 5(8):1035-1045 (1996); S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and S. P. Arneric, M. W. Holladay, J. P. Sullivan, "Cholinergic channel modulators as a novel therapeutic strategy for Alzheimer's disease" Exp. Opin. Invest. Drugs 5(1):79-100 (1996).

Compounds that bind to the nicotinic acetylcholine receptor can be used to treat anxiety as described by M. Williams and S. P Arneric, "Beyond the Tobacco Debate: dissecting out the therapeutic potential of nicotine" Exp. Opin. Invest. Drugs 5(8):1035-1045 (1996); S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and S. P. Arneric, M. W. Holladay, J. P. Sullivan, "Cholinergic channel modulators as a novel therapeutic strategy for Alzheimer's disease" Exp. Opin. Invest. Drugs 5(1): 79-100 (1996).

Compounds that bind to the nicotinic acetylcholine receptor can be used to treat depression as described by S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Compounds that bind to the nicotinic acetylcholine receptor can be used to treat mania and schizophrenia can be demonstrated by M. Williams and S. P Arneric, "Beyond the Tobacco Debate: dissecting out the therapeutic potential of nicotine" Exp. Opin. Invest. Drugs 5(8):1035-1045 (1996); S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat anorexia and other eating disorders as described by M. Williams and S. P Arneric, "Beyond the Tobacco Debate: dissecting out the therapeutic potential of nicotine" Exp. Opin. Invest. Drugs 5(8):1035-1045 (1996); S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat AIDS-induced dementia as described by M. Williams and S. P Arneric, "Beyond the Tobacco Debate: dissecting out the therapeutic potential of nicotine" Exp. Opin. Invest. Drugs 5(8):1035-1045 (1996); S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat epilepsy as described by M. Williams and S. P Arneric, "Beyond the Tobacco Debate: dissecting out the therapeutic potential of nicotine" Exp. Opin. Invest. Drugs 5(8):1035-1045 (1996); S. P. Arneric, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995); and J. Lindstrom, "Nicotinic Acetylchloline Receptors in Health and Disease" Molecular Neurobiology 15:193-222 (1997).

Compounds that bind to the nicotinic acetylcholine receptor can be used to treat urinary incontinence as described by M. Williams and S. P Arneric, "Beyond the Tobacco Debate: dissecting out the therapeutic potential of nicotine" Exp. Opin. Invest. Drugs 5(8):1035-1045 (1996).

Compounds that bind to the nicotinic acetylcholine receptor can be used to treat premenstrual syndrome can be demonstrated by M. Williams and S. P Arneric, "Beyond the Tobacco Debate: dissecting out the therapeutic potential of nicotine" Exp. Opin. Invest. Drugs 5(8):1035-1045 (1996); and S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Compounds that bind to the nicotinic acetylcholine receptor can be used to treat substance abuse as described by M. Williams and S. P Americ, "Beyond the Tobacco Debate: dissecting out the therapeutic potential of nicotine" Exp. Opin. Invest. Drugs 5(8):1035-1045 (1996); and S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Compounds that bind to the nicotinic acetylcholine receptor can be used to treat smoking cessation as described by M. Williams and S. P Americ, "Beyond the Tobacco Debate: dissecting out the therapeutic potential of nicotine" Exp. Opin. Invest. Drugs 5(8):1035-1045 (1996); and S. P. Americ, J. P. Sullivan, M. Williams, "Neuronal nicotinic acetylcholine receptors. Novel targets for central nervous system theraputics" Psychopharmacology: The Fourth Generation of Progress. F. E. Bloom and D. J. Kupfer (Eds.), Raven Press, New York 95-109 (1995).

Compounds that bind to the nicotinic acetylcholine receptor can be used to treat inflammatory bowel syndrome. M. Williams and S. P Americ, "Beyond the Tobacco Debate: dissecting out the therapeutic potential of nicotine" Exp. Opin. Invest. Drugs 5(8):1035-1045 (1996); and J. Lindstrom, "Nicotinic Acetylchloline Receptors in Health and Disease" Molecular Neurobiology 15:193-222 (1997).

The present invention also provides pharmaceutical compositions that comprise (1S,5S)-3-(5,6-dichloropyridin-3-yl)-3,6-diazabicyclo[3.2.0]heptane benzenesulfonate. The pharmaceutical compositions comprise (1S,5S)-3-(5,6-dichloropyridin-3-yl)-3,6-diazabicyclo[3.2.0]heptane benzenesulfonate formulated together with one or more nontoxic pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of (1S,5S)-3-(5,6-dichloropyridin-3-yl)-3,6-diazabicyclo[3.2.0]heptane benzenesulfonate, it is desirable to slow the absorption of the (1S,5S)-3-(5,6-dichloropyridin-3-yl)-3,6-diazabicyclo[3.2.0]heptane benzenesulfonate from subcutaneous or intramuscular injection. This can be accomplished by the use of a liquid suspension of crystalline or amorphous material with poor water solubility. The rate of absorption of (1S,5S)-3-(5,6-dichloropyridin-3-yl)-3,6-diazabicyclo[3.2.0]heptane benzenesulfonate then depends upon its rate of dissolution which, in turn, may depend upon crystal size and crystalline form. Alternatively, delayed absorption of a parenterally administered (1S,5S)-3-(5,6-dichloropyridin-3-yl)-3,6-diazabicyclo[3.2.0]heptane benzenesulfonate is accomplished by dissolving or suspending (1S,5S)-3-(5,6-dichloropyridin-3-yl)-3,6-diazabicyclo[3.2.0]heptane in an oil vehicle benzenesulfonate.

Injectable depot forms are made by forming microencapsule matrices of the drug in biodegradable polymers such as polylactide-polyglycolide. Depending upon the ratio of (1S,5S)-3-(5,6-dichloropyridin-3-yl)-3,6-diazabicyclo[3.2.0]heptane benzenesulfonate to polymer and the nature of the particular polymer employed, the rate of (1S,5S)-3-(5,6-dichloropyridin-3-yl)-3,6-diazabicyclo[3.2.0]heptane benzenesulfonate release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, (1S,5S)-3-(5,6-dichloropyridin-3-yl)-3,6-diazabicyclo[3.2.0]heptane benzenesulfonate may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

(1S,5S)-3-(5,6-dichloropyridin-3-yl)-3,6-diazabicyclo[3.2.0]heptane benzenesulfonate can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to (1S,5S)-3-(5,6-dichloropyridin-3-yl)-3,6-diazabicyclo[3.2.0]heptane benzenesulfonate, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to (1S,5S)-3-(5,6-dichloropyridin-3-yl)-3,6-diazabicyclo[3.2.0]heptane benzenesulfonate, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing (1S,5S)-3-(5,6-dichloropyridin-3-yl)-3,6-diazabicyclo[3.2.0]heptane benzenesulfonate with suitable non-irritating carriers or carriers such as cocoa butter, polyethylene glycol or a suppository wax which are solid at room temperature but liquid at body temperature and therefore melt in the rectum or vaginal cavity and release (1S,5S)-3-(5,6-dichloropyridin-3-yl)-3,6-diazabicyclo[3.2.0]heptane benzenesulfonate.

(1S,5S)-3-(5,6-dichloropyridin-3-yl)-3,6-diazabicyclo[3.2.0]heptane benzenesulfonate can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to (1S,5S)-3-(5,6-dichloropyridin-3-yl)-3,6-diazabicyclo[3.2.0]heptane benzenesulfonate, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of (1S,5S)-3-(5,6-dichloropyridin-3-yl)-3,6-diazabicyclo[3.2.0]heptane benzenesulfonate include powders, sprays, ointments and inhalants. (1S,5S)-3-(5,6-dichloropyridin-3-yl)-3,6-diazabicyclo[3.2.0]heptane benzenesulfonate may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Actual dosage levels of (1S,5S)-3-(5,6-dichloropyridin-3-yl)-3,6-diazabicyclo[3.2.0]heptane benzenesulfonate in the pharmaceutical compositions of this invention can be varied so as to obtain an amount of (1S,5S)-3-(5,6-dichloropyridin-3-yl)-3,6-diazabicyclo[3.2.0]heptane benzenesulfonate which is effective to achieve the desired therapeutic response for a particular patient, compositions and mode of administration. The selected dosage level will depend upon the activity of (1S,5S)-3-(5,6-dichloropyridin-3-yl)-3,6-diazabicyclo[3.2.0]heptane benzenesulfonate, the route of administration, the severity of the condition being treated and the condition and prior medical history of the patient being treated.

When used in the above or other treatments, a therapeutically effective amount of (1S,5S)-3-(5,6-dichloropyridin-3-yl)-3,6-diazabicyclo[3.2.0]heptane benzenesulfonate can be employed in pure form or, where such forms exist, in pharmaceutically acceptable salt, ester or prodrug form. The phrase "therapeutically effective amount" of (1S,5S)-3-(5,6-dichloropyridin-3-yl)-3,6-diazabicyclo[3.2.0]heptane benzenesulfonate means a sufficient amount of the compound to treat disorders, at a reasonable benefit/risk ratio applicable to any medical treatment. It will be understood, however, that the total daily usage of (1S,5S)-3-(5,6-dichloropyridin-3-yl)-3,6-diazabicyclo[3.2.0]heptane benzenesulfonate and compositions of the present invention will be decided by the attending physician within the scope of sound medical judgement. The specific therapeutically effective dose level for any particular patient will depend upon a variety of factors including the disorder being treated and the severity of the disorder; activity of (1S,5S)-3-(5,6-dichloropyridin-3-yl)-3,6-diazabicyclo[3.2.0]heptane benzenesulfonate; the specific composition employed; the age, body weight, general health, sex and diet of the patient; the time of administration, route of administration, and rate of excretion of (1S,5S)-3-(5,6-dichloropyridin-3-yl)-3,6-diazabicyclo[3.2.0]heptane benzenesulfonate; the duration of the treatment; drugs used in combination or coincidental with (1S,5S)-3-(5,6-dichloropyridin-3-yl)-3,6-diazabicyclo[3.2.0]heptane benzenesulfonate; and like factors well known in the medical arts.

The present invention contemplates formation of (1S,5S)-3-(5,6-dichloropyridin-3-yl)-3,6-diazabicyclo[3.2.0]heptane benzenesulfonate by synthetic means or formation by in vivo biotransformation.

The total daily dose of (1S,5S)-3-(5,6-dichloropyridin-3-yl)-3,6-diazabicyclo[3.2.0]heptane benzenesulfonate administered to a human or lower animal may range from about 0.001 to about 1000 mg/kg/day. For purposes of oral administration, more preferable doses can be in the range of from about 0.1 to about 50 mg/kg/day. If desired, the effective daily dose can be divided into multiple doses for purposes of administration; consequently, single dose compositions may contain such amounts or submultiples thereof to make up the daily dose.

What is claimed is:

1. A process for preparing (1S,5S)-3-(5,6-dichloropyridin-3-yl)-3,6-diazabicyclo[3.2.0]heptane benzenesulfonate comprising treating tert-butyl (1R,5S)-3-(5,6-dichloropyridin-3-yl)-3,6-diazabicyclo[3.2.0]heptane-6-carboxylate with benzenesulfonic acid.

* * * * *